(12) United States Patent
Dumonceaux et al.

(10) Patent No.: US 10,385,338 B2
(45) Date of Patent: Aug. 20, 2019

(54) TREATMENT OF FACIOSCAPULOHUMERAL DYSTROPHY

(71) Applicants: ASSOCIATION INSTITUT DE MYOLOGIE, Paris (FR); INSTITUT NATIONAL DE LA SANTE ET DE LA RECHERCHE MEDICALE, Paris (FR); SORBONNE UNIVERSITE, Paris (FR); CENTRE NATIONAL DE LA RECHERCHE SCIENTIFIQUE, Paris (FR)

(72) Inventors: Julie Dumonceaux, Joinville-le-pont (FR); Thomas Voit, London (GB); Virginie Mariot, Paris (FR)

(73) Assignees: ASSOCIATION INSTITUT DE MYOLOGIE, Paris (FR); INSTITUT NATIONAL DE LA SANTE ET DE LA RECHERCHE MEDICALE, Paris (FR); SORBONNE UNIVERSITE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/549,072

(22) PCT Filed: Feb. 8, 2016

(86) PCT No.: PCT/EP2016/052652
§ 371 (c)(1),
(2) Date: Aug. 4, 2017

(87) PCT Pub. No.: WO2016/124793
PCT Pub. Date: Aug. 11, 2016

(65) Prior Publication Data
US 2018/0016577 A1    Jan. 18, 2018

(30) Foreign Application Priority Data
Feb. 6, 2015 (EP) ..................... 15305184

(51) Int. Cl.
| | |
|---|---|
| A61K 48/00 | (2006.01) |
| C07H 21/02 | (2006.01) |
| C07H 21/04 | (2006.01) |
| C12N 15/113 | (2010.01) |
| A61K 31/713 | (2006.01) |

(52) U.S. Cl.
CPC .......... *C12N 15/113* (2013.01); *A61K 31/713* (2013.01); *C12N 2310/13* (2013.01); *C12N 2310/3183* (2013.01); *C12N 2310/346* (2013.01); *C12N 2310/532* (2013.01)

(58) Field of Classification Search
CPC ............ C12N 2310/321; C12N 15/113; A61K 31/713
See application file for complete search history.

(56) References Cited

FOREIGN PATENT DOCUMENTS

| WO | 2012/024535 A2 | 2/2012 |
|---|---|---|
| WO | 2013/016352 A1 | 1/2013 |
| WO | 2013/019623 A2 | 2/2013 |

OTHER PUBLICATIONS

Geng et al: "DUX4 Activates Germline Genes, Retroelements, and Immune Mediators: Implications for Facioscapulohumeral Dystrophy", Developmental Cell, vol. 22, No. 1 (Jan. 1, 2012), pp. 38-51.
Young et al: "DUX4 Binding to Retroelements Creates Promoters That Are Active in FSHD Muscle and Testis", PLOS Genetics, vol. 9, No. 11 (Nov. 21, 2013), p. e1003947.
European Patent Office, International Search Report in PCT/EP2016/052652, dated Apr. 19, 2016.

*Primary Examiner* — Amy H Bowman
(74) *Attorney, Agent, or Firm* — Arrigo, Lee, Guttman & Mouta-Bellum LLP

(57) ABSTRACT

The present invention relates to nucleic acids, compositions and methods for the treatment of facioscapulohumeral dystrophy.

20 Claims, 11 Drawing Sheets
Specification includes a Sequence Listing.

Decoy 3

G*C*G*U*G*A*U*A*A*cctGTGGGAGGCAGAGATGGAGGCAGA*A*U*C*C*A*U*G*C
C*G*C*A*U*G*C*U*A*T*ggaCACCCTCCGTCggaCACCCTCCGTCU*U*A*G*U*A*C*G Mut     C     T     G         C     T     G Decoy inserted into the AAV genome:

CCTGTGGGAGGTAATCCAATCATGGAGGCAGCCTGTGGGAGGTAATCCAATCATGGAGGCA

TREATMENT OF FACIOSCAPULOHUMERAL DYSTROPHY

SEQUENCE LISTING

The instant application contains a Sequence Listing which has been submitted electronically in ASCII format and is hereby incorporated by reference in its entirety. Said ASCII copy, created on Jul. 31, 2017, is named B1964PC00-SEQ_LIST_ST25.txt and is 6,249 bytes in size.

The present invention relates to nucleic acids, compositions and methods for the treatment of facioscapulohumeral dystrophy.

BACKGROUND OF THE INVENTION

Facioscapulohumeral dystrophy (FSHD) is one of the most common inherited muscular dystrophies. The pathology is caused by a loss of epigenetic marks within the D4Z4 macrosatellite located in the sub-telomeric region of chromosome 4 leading to chromatin relaxation (1). In 95% of the FSHD patients (named FSHD1), this chromatin relaxation is associated with a contraction of the D4Z4 array (2). In the general population, this region is normally composed of 11 to 150 D4Z4 repeats, whereas FSHD1 patients only carry 1 to 10 repeats (3). The remaining 5% of the FSHD patients do not present a contraction of D4Z4 but 85% of them carry a mutation in the epigenetic modifier gene SMCHD1 (4). SMCHD1 is located on chromosome 18 and in most of the FSHD2 patients, the mutations lead to either a haploinsufficiency or a dominant negative mutations in SMCDH1 protein, leading to a reduced binding of SMCHD1 protein to the D4Z4 repeat and consequently to a loss of epigenetic marks in this region (4). In conclusion and despite the fact that 2 independent loci of the disease have been characterized, both FSHD1 and FSHD2 patients are undistinguishable and share a hypomethylation of D4Z4 on chromosome 4. This chromatin relaxation alone is not sufficient to trigger the disease and must be associated with a permissive chromosome 4 characterized by: (i) the presence of a permissive Stable Simple Sequence Length polymorphism (SSLP) located upstream D4Z4 (5-7). At least 12 different haplotypes have been characterized but only several are associated with FSHD (7, 8). These sequence variations may be important for the chromatin conformation but their exact roles in FSHD onset are unknown. (ii) the presence of a 4qA region containing a pLAM polyadenylation site distal to the last D4Z4 repeat allowing the stabilization of the DUX4 mRNA by the poly(A) tail (5, 9). Indeed, each D4Z4 repeat contains the open reading frame of a transcription factor named DUX4 (10, 11) and the chromatin relaxation results in an inefficient repression of this double homeobox gene in both FSHD1 and FSHD2. DUX4 is a transcription factor and DUX4-induced gene expression is the major molecular signature in FSHD skeletal muscles (12).

There is currently no effective treatment available for FSHD. A treatment of FSHD by preventing or inhibiting the expression of the DUX4 transcription factor has been proposed in application WO 2013/016352 using RNA interference based methods. However, direct gene inactivation methods using antisense technology or DNA-based gene deactivation through DNA enzyme cutting technologies (meganucleases, zinc finger nucleases, TALENs or others) may work well on FSHD patient cells but predictably will have low efficacy in vivo in the human. This is due to the fact that DUX4 gene transcription occurs haphazardly in a few myonuclei only at first. Subsequently neighbouring myonuclei are subject to the poison DUX4 protein effect modifying their gene expression (13). As a consequence of this poison peptide mechanism, whole organ- (and not cell-)treatment approaches will need to achieve a very high in tissue biodistribution in order to effectively inactivate DUX4 protein-transcribing myonuclei. This cannot be achieved at the present time where tissue biodistribution of OAN molecules or DNA cutting enzymes remains low (lit). In consequence, the method exposed herein targets the neutralization of the poison peptide DUX4 rather than the inactivation of the DUX4 gene.

In any case, no treatment is currently available for the FSHD patient. Therefore, an urgent need exists for providing a treatment of FSHD.

SUMMARY OF THE INVENTION

The present inventors herein show that use of decoy nucleic acid containing at least one binding site for the DUX4 transcription factor protein is efficient in blocking transcription of DUX4 target genes. FSHD is a disease caused by DUX4 expression in tissue or cells where it should not normally be expressed, and downstream expression of DUX4 target genes that are otherwise not expressed to the same degree under non-pathological conditions. Therefore the nucleic acids designed by the inventors represent a very powerful therapeutic tool for the treatment of FSHD.

Accordingly, a first object of the invention is a decoy nucleic acid which can inhibit DUX4-mediated gene activation by binding to the DNA binding site of the DUX4 transcription factor protein.

Another object of the invention is a vector comprising such a decoy nucleic acid, in particular a viral vector harboring a decoy nucleic acid according to the invention.

Another object of the invention relates to a recombinant cell comprising a decoy nucleic acid according to the invention, and a non-human animal comprising such a cell.

Furthermore, the invention also relates to a decoy nucleic acid binding the DUX4 transcription factor protein, for use as a medicament.

In particular, the invention specifically relates to a method for the treatment of FSHD in a subject in need thereof, comprising administering to said subject a decoy nucleic acid molecule, a vector or a cell according to the invention.

Another object of the invention is a method to inhibit in vitro the gene regulation activity of of the DUX4 transcription factor protein through interference with its DNA binding site(s).

Further objects and embodiments are provided in the following detailed description of the invention.

DETAILED DESCRIPTION OF THE INVENTION

In the context of the present invention, the term "decoy nucleic acid" denotes a nucleic acid that is able to bind the DUX4 transcription factor protein in a sequence-specific way and blocks the ability of the DUX4 transcription factor protein to act on a DUX4 responsive gene. Without wishing to be bound by any theory, it is expected that the decoy nucleic acid molecule of the present invention acts by competitively inhibiting the binding of DUX4 to its target binding site(s) present in DUX4 responsive (or target) genes. Representative DUX4 responsive genes include, without limitation, ZSCAN4, TRIM43, and MBD3L2. A person skilled in the art is thus able to assess the decoy efficiency of a nucleic acid molecule by assessing the expression of these proteins in a cell transfected with a nucleic acid molecule of the invention, or transduced with a viral vector harboring such a decoy nucleic acid molecule. Other means for determining the decoy activity of a nucleic acid molecule of the invention include the use of reporter assay, where a reporter gene such as GFP is placed under the control of a promoter of a gene responsive to the DUX4 transcription factor.

The decoy nucleic acid molecule of the invention comprises at least one DUX4 binding site. DUX4 binding sites are known in the art, such as those previously described in Geng et al, 2012 (14). Representative DUX4 binding sites include the minimum sequences of the DUX4 binding motif in nonrepetetive elements and MaLR-associated sites which are TAAYYBAATCA (SEQ ID NO:1) and TAAYBYAATCA (SEQ ID NO:2) respectively (according to IUPAC nomenclature, wherein Y denotes C or T, and B denotes C or G or T). Of course, in the present invention, any sequence which may be bound by the DUX4 transcription factor protein may be used.

In a particular embodiment, the DUX4 binding site is selected in the group consisting of TAACCCAATCA (SEQ ID NO:3), TAATTTAATCA (SEQ ID NO:4), TAATCCAATCA (SEQ ID NO:5) and TAATTGAATCA (SEQ ID NO:6). In a particular embodiment, the DUX4 binding site is TAATCCAATCA (SEQ ID NO:5).

The decoy nucleic acid of the invention may comprise one or more than one DUX4 binding sites. In a preferred embodiment, the decoy nucleic acid of the invention comprises more than one DUX4 binding sites, such as two, three, four, five, six, seven or even more than seven DUX4 binding sites. In this embodiment wherein the decoy nucleic acid comprises more than one DUX4 binding sites, each binding site is selected independently from the other. In other terms, the multiple DUX4 binding sites present in the decoy nucleic acid of the invention may be all the same, or all different, or several of the binding sites have the same first sequence while other binding sites may be of a sequence or sequences different from the first sequence.

In case of a decoy nucleic acid containing more than one DUX4 binding sites, said binding sites are separated, or may or may not be separated by one or more nucleotides that are not part of the binding site. Such nucleotides are also herein referred to as "spacers". Such spacers, if present, may include one or more nucleotides, such as 1, 2, 3, 4, 5, 6, 7, 8, 9, 10, 11, 12, 13, 14, 15, 16, 17, 18, 19, 20 or more than 20 nucleotides. In a particular embodiment, the spacer or spacers are comprised of random nucleotides.

In a particular embodiment, the decoy nucleic acid of the invention comprises or consists of a double-stranded sequence selected from:

(SEQ ID NO: 7)
GTAATCCAATCAT;

(SEQ ID NO: 8)
GAGGTAATCCAATCATGGA;

(SEQ ID NO: 9)
CGTAATCCAATCAGC;

(SEQ ID NO: 10)
TGCGTAATCCAATCAGCGT;

(SEQ ID NO: 11)
CCTGTGGGAGGTAATCCAATCATGGAGGCAGCCTGTGGGAGGTAATCCAATCATGGAGGCAGA;

(SEQ ID NO: 12)
GCGUACGAUACCTGTGGGAGGTAATCCAATCATGGAGGCAGCCTGTGGGAGGTAATCCAATCATGGAGGCAGAAUCCCAUGC;

(SEQ ID NO: 13)
GTGGGAGGTAATCCAATCATGGAGGCAG;

(SEQ ID NO: 14)
CCCATGCGTAATCCAATCAGCGTACGAT;

(SEQ ID NO: 15)
CCTGTGGGAGGTAATCCAATCATGGAGGCAGCCT;
and (SEQ ID NO: 16)
GACCCTGTGGGAGGTAATCCAATCATGGAGGCAGTTTCCC.

In a further particular embodiment, the decoy nucleic acid of the invention comprises or consists of a double-stranded sequence selected from:

(SEQ ID NO: 23)
CCCATGCGTAATCCAATCAGCGTACGAT

According to a particular embodiment, the present invention implements an oligonucleotide comprising, or consisting of, any of decoy-1, -2, -3, -4, -5, -6, -7, -8, -9, -10 or -11 as described in the experimental section.

According to a particular embodiment, the oligonucleotide according to the invention comprises or consists of a double stranded sequence selected in the group consisting of SEQ ID NO:7 to SEQ ID NO:16 and SEQ ID NO:23. In a further particular embodiment, the oligonucleotide according to the invention is selected in the group consisting of SEQ ID NO:7 to SEQ ID NO:16 and SEQ ID NO:23.

In order for the DUX transcription factor protein to be able to recognize and bind to the decoy nucleic acid of the invention, this decoy nucleic has to have a double-stranded structure. Therefore, the decoy may be composed of two hybridized complementary single stranded sequences, or may be an isolated sequence which comprises two complementary regions such that the oligonucleotide can form a self-complementary double-stranded molecule. In addition, the double-stranded structure may be obtained using linkers within a single-stranded oligonucleotide, such as hexaethyleneglycol linkers, wherein the oligonucleotide is a self-complementary oligonucleotide comprising two regions able to hybridize one with the other (representative oligonucleotides corresponding to this definition include decoy-4, -5, -6 and -9 represented in FIGS. 1 and 6).

In a particular embodiment, the decoy nucleic acid of the invention comprised of a self-complementary double-stranded molecule is designed such that it may form a double-stranded portion comprising the sequence of any one of SEQ ID NO: 7 to 16 and SEQ ID NO: 23. For illustrative purpose of this embodiment, and as shown in FIGS. 1 and 6:

the single-stranded oligonucleotide of SEQ ID NO:24 is self-complementary and is able to form a double-stranded portion comprising the sequence shown in SEQ ID NO: 13 or SEQ ID NO:15;

the single-stranded oligonucleotide of SEQ ID NO:20 is self-complementary and is able to form a double-stranded portion comprising the sequence shown in SEQ ID NO: 13 or SEQ ID NO:16.

Illustrative embodiments of the decoy nucleic acid of the invention comprised of a self-complementary double-stranded molecule include:

(SEQ ID NO: 24)
CTGCCTCCATGATTGGATTACCTCCCACAGG\*\*\*CCTGTGGGAGGTAATC

CAATCATGGAGGCAGCCT\*\*\*AGG (SEQ ID NO: 20)
AAACTGCCTCCATGATTGGATTACCTCCCACAGGGTCTTTTGACCCTGTG

GGAGGTAATCCAATCATGGAGGCAGTTTCCCTTTTGGG (SEQ ID NO: 25)
AAACTGCCTCCATGATTGGATTACCTCCCACAGGGTC\*\*\*GACCCTGTGG

GAGGTAATCCAATCATGGAGGCAGTTTCCC\*\*\*GGG (SEQ ID NO: 26)
CTGCCTCCATGATTGGATTACCTCCCACTTTTGTGGGAGGTAATCCAATC

ATGGAGGCAGTTTTCTGC (SEQ ID NO: 27)
TACGCTGATTGGATTACGCATGGGTTTTCCCATGCGTAATCCAATCAGCG

TACGATTTTTATCG wherein \*\*\* represents a linker such as a hexaethyleneglycol.

Alternatively, in the single-stranded self-complementary oligonucleotides having one or more linkers therein, such as in SEQ ID NO:24 and 25, the linker (represented by "\*\*\*" above) may be a nucleotide linker such as a TTTT linker.

The oligonucleotide of the invention may be of any suitable type. Representative oligonucleotide types include oligodeoxyribonucleotides, oligoribonucleotides, morpholinos, 2'-O-methyl ribonucleotides, tricyclo-DNA-antisense oligonucleotides, tricyclo-phosphorothioate DNA oligonucleotides, LNA, small nuclear RNA-modified such as U7-, U1- or U6-modified AONs (or other UsnRNPs), or conjugate products thereof such as peptide-conjugated or nanoparticle-complexed oligonucleotides.

The oligonucleotide of the invention may also be comprised of a combination of different oligonucleotide chemistries. For example, chemistries different from the deoxyribonucleotide chemistry may be introduced at one or both ends of the decoy nucleic acid of the invention to improve its stability. For example, the oligonucleotide of the invention may comprise one or more parts including 2'-O-methyl ribonucleotides and other parts containing deoxyribonucleotides. In a preferred embodiment, the oligonucleotide of the invention comprises a first nucleic acid sequence which comprises at either or both of its ends one or more consecutive oligonucleotide types different from the deoxyribonucleotide chemistry (such as any one chemistry described in the preceding paragraph), such as 2'-O-methyl ribonucleotides, such as 1, 2, 3, 4, 5, 6, 7, 8, 9, 10 or more than 10 consecutive 2'-O-methyl ribonucleotides, and which comprises a deoxyribonucleotide part between these other chemistries parts, such as 2'-O-methyl ribonucleotide parts, thereby protecting the deoxyribonucleotide part of the oligonucleotide at each of its extremities, and wherein the DUX4 site(s) is(are) comprised within the deoxyribonucleotide part of the oligonucleotide. Such oligonucleotides include:

(SEQ ID NO: 17)
<u>GAG</u>GTAATCCAATCATG<u>GGA</u>;

(SEQ ID NO: 18)
<u>UGC</u>GTAATCCAATCAGC<u>GU</u>;

(SEQ ID NO: 19)
<u>GCGUACGAUA</u>CCTGTGGGAGGTAATCCAATCATGGAGGCAGCCTGTGGGA

GGTAATCCAATCATGGAGGCAG<u>AAUCCCAUGC</u>, and (SEQ ID NO: 20)
<u>AAA</u>CTGCCTCCATGATTGGATTACCTCCCACAGGGTCTTTTGACCCTGTG GGAGGTAATCCAATCATGGAGGCAGTTTCCCTTTTG<u>GG</u>;

wherein the underlined nucleotides represent 2'-O-methyl ribonucleotides.

In addition, the internucleoside bonds may be of any suitable type, such as a phosphodiester internucleoside linkage or a phosphorothioate internucleoside linkage. The oligonucleotide of the invention may further comprise different types of internucleoside linkages along the molecule. For example, a part of the nucleosides may be linked with phosphorothioate internucleoside linkages while another part may be linked with phosphodiester internucleoside linkages. Representative nucleotides comprising mixed phosphorothioate and phosphodiester linkages include:

<u>G\*C\*G\*(U/dT)\*A\*C\*G\*A\*(U/dT)\*A</u>\*CCTGTGGGAGGTAATCCAAT

CATGGAGGCAGCCTGTGGGAGGTAATCCAATCATGGAGGCAG<u>A\*A\*(U/</u>

<u>dT)\*C\*C\*C\*A\*(U/dT)\*G\*C</u>

(SEQ ID NO:19 above; decoy-3 in the examples and FIG. 1 together with its complementary strand); and <u>A\*A\*A</u>CTGCCTCCATGATTGGATTACCTCCCACAGGGTCTTTTGACCCTG TGGGAGGTAATCCAATCATGGAGGCAGTTTCCCTTTT<u>G\*G\*G</u>

(SEQ ID NO:20 above; decoy-7 in the examples and FIG. 1, this oligonucleotide being a single stranded self-complementary oligonucleotide whose double-stranded structure is formed of SEQ ID NO:16);
wherein \* indicates phosphorothioate bonds and wherein the underlined oligonucleotides are deoxyribonucleotides or 2'-O-methyl ribonucleotides.

These modifications may be advantageous in that they allow protecting the decoy oligonucleotide from degradation through DNA cutting enzymes. Other means to protect the oligonucleotide include the addition of ITR sequences, or the ligation of the oligonucleotide to proteins.

Isolated oligonucleotides employed in the practice of the invention are generally from about 10 to about 150 nucleotides in length, and may be for example, about 10, or about 15, or about 20 or about 30, or about 40, or about 50, or about 60, or about 80, or about 90, or about 100, or about 110, or about 120, or about 130 or about 140, or about 150 nucleotides or more in length depending on the number of DUX4 binding sites and the size of the spacers included in the oligonucleotide, but also on the chemistry of the oligonucleotide.

For example, the nucleic acid decoy of the invention may include a double-stranded portion (be it formed from two annealed single stranded oligonucleotides, or from a single self-complementary double-stranded oligonucleotide, as described above) comprising from 13 to 150 nucleotides in length, such as of about 13, 14, 15, 16, 17, 18, 19, 20, 21, 22, 23, 24, 25, 26, 27, 28, 29, 30, 31, 32, 33, 34, 35, 36, 37, 38, 39, 40 or more than 40 nucleotides in length.

Furthermore, according to another embodiment, the decoy nucleic acid of the invention is comprised within a vector. According to the present invention, a "vector" is any suitable vehicle capable of facilitating the transfer of the decoy nucleic acid of the invention to a target cell. Suitable vectors include plasmids, phagemids, viruses and any other suitable vehicle. Such vector may in particular include plasmid vectors or viral vectors.

Viral vectors are a preferred type of vectors. They may be derived from a lentivirus such as HIV-1, a retrovirus, such as moloney murine leukemia virus, an adenovirus, an adeno-associated virus; SV40-type viruses; Herpes viruses such as HSV-1 and a vaccinia virus. One can readily employ other vectors not named but known in the art. Among the vectors that have been validated for clinical applications and that can be used to deliver the antisense sequences, lentivirus, retrovirus and AAV show a greater potential for transducing relevant target cells. In a particular embodiment of the invention, the target cell is a cell of the muscular lineage, such as a myoblast, or a myotube, or a mature myofibre. In a further embodiment, the vector used for targeting said cell of the muscular lineage is a lentivirus or an AAV.

When the decoy nucleid acid of the invention is incorporated into a vector, said nucleic acid may be of a length compatible with said vector, and the size is not so limited as when using an oligonucleotide for implementing the invention. Thanks to this embodiment, the vector may comprise any number of DUX4 binding sites that it is possible to introduce within the vector taking into account its size limitations. For example, the present invention envisions the implementation of concatemers containing multiple DUX4 binding sites. These multiple DUX4 binding sites may comprise a unique DUX4 binding sequence or binding sites of different sequences. Thanks to this approach, a great number of DUX4 decoys may be introduced within the target cell thus effecting a potent DUX4 transcription factor inactivation.

For example, the vector, such as viral vector like a lentiviral vector or an AAV vector, may carry 1, 2, 3, 4, 5 or more than 5 copies of a sequence comprising DUX4 binding sites such as the sequence (SEQ ID NO: 21)
TCGAGAATAACCCAATCAAATTAATTTAATCATAATCCAATCAAGATAAT

TGAATCATGGTAATTGAATCAGGTAATTGAATCATGGTAATCCAATCAC, the sequence (SEQ ID NO: 22)
TCGAGTAATTTAATCAGCGTACGATAATCCCATGCGTAATCCAATCAGCG

TACGATAATCCCATGCGTAATCCAATCAGCGTACGATAATCCCATGCGC or the sequence (SEQ ID NO: 28)
CCTGTGGGAGGTAATCCAATCATGGAGGCAGCCTGTGGGAGGTAATCCAA

TCATGGAGGCAG.

The invention further relates to a vector, in particular a viral vector such as a lentiviral or AAV vector, comprising a decoy nucleic acid including one or more binding sites for a transcription factor protein. In a particular embodiment, the vector comprises 1, 2, 3, 4, 5 or more than 5 binding sites for a transcription factor, such as binding sites for the DUX4 transcription factor. In another embodiment, the vector comprises more than 10, 20, 30, 40, 50, 60, 70, 80, 90, 100, 150, 200, 250, 300, 350, 400, 450, 500, 550, 600, 650 or even more than 700 binding sites, such as binding sites for the DUX4 transcription factor.

The invention also relates to a pharmaceutical composition comprising a decoy nucleic acid of the invention, in particular in the form of an oligonucleotide or included into a vector, in particular a viral vector such as, for example, a lentiviral vector. In addition to the oligonucleotide or to the vector, a pharmaceutical composition of the present invention may also include a pharmaceutically or physiologically acceptable carrier such as saline, sodium phosphate, etc. The composition will generally be in the form of a liquid, although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, celluose, water syrup, methyl cellulose, methyl and propylhydroxybenzoates, mineral oil, etc. The formulation can also include lubricating agents, wetting agents, emulsifying agents, preservatives, buffering agents, etc. In particular, the present invention involves the administration of an oligonucleotide and is thus somewhat akin to gene therapy. Those of skill in the art will recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

The compositions of the invention are generally administered via enteral or parenteral routes, e.g. intravenously (i.v.), intra-arterially, subcutaneously, intramuscularly (i.m.), intracerebrally, intracerebroventricularly (i.c.v.), intrathecally (i.t.), intraperitoneally (i.p.), although other types of administration are not precluded.

Injectable preparations, for example, sterile injectable aqueous or oleaginous suspensions may be formulated according to the known art using suitable dispensing or wetting agents and suspending agents. The sterile injectable preparation can also be a sterile injectable solution or suspension in a nontoxic parenterally acceptable diluent or solvent, for example, as a solution in 1,3-butanediol. While delivery may be either local (i.e. in situ, directly into tissue such as muscle tissue) or systemic, usually delivery will be local to affected muscle tissue, e.g. to skeletal muscle, smooth muscle, heart muscle, etc. Depending on the form of the oligonucleotides or vectors that are administered and the tissue or cell type that is targeted, techniques such as electroporation, sonoporation, a "gene gun" (delivering nucleic acid-coated gold particles), etc. may be employed.

One skilled in the art will recognize that the amount of an oligonucleotide or of a vector containing a decoy nucleid acid according to the invention to be administered will be an amount that is sufficient to induce amelioration of FSHD symptoms or even treatment of the disease. Such an amount may vary inter alia depending on such factors as the gender, age, weight, overall physical condition of the patient, etc. and may be determined on a case by case basis. The amount may also vary according to other components of a treatment protocol (e.g. administration of other medicaments, etc.). Generally, a suitable dose is in the range of from about 0.1 mg/kg to about 100 mg/kg, and more usually from about 2 mg/kg/day to about 10 mg/kg. If a viral-based delivery of the decoy nucleic acid is chosen, suitable doses will depend on different factors such as the virus that is employed, the route of delivery (intramuscular, intravenous, intra-arterial or other), but may typically range from $10^9$ to $10^{15}$ viral particles/kg. Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the patient. In addition, treatment of the patient may be a single event, or the patient is administered with the oligonucleotide or the vector on multiple occasions, that may be, depending on the results obtained, several days apart, several weeks apart, or several months apart, or even several years apart.

Further aspects and advantages of the present inventions will be disclosed in the following experimental section, which shall be considered as illustrative only, and not limiting the scope of this application.

The decoys are double strand DNA synthetized either as one single DNA strand (Decoy-4 (SEQ ID NO:29); Decoy-5 (SEQ ID NO:30); Decoy-6 (SEQ ID NO:24); and Decoy-7 (SEQ ID NO:20)) or as 2 oligonucleotides which are hybridized together (Decoy-1 (SEQ ID NO:17 & SEQ ID NO:32); Decoy-2 (SEQ ID NO:18 & SEQ ID NO:33); and Decoy-3 (SEQ ID NO:19 & SEQ ID NO:34)). Chemical modifications are: * 2'Omethyl modifications with phosphorothioate linkage. Underlined bases carry phosphorothioate linkage. The hexaethyleneglycol linkers are represented by gray brackets. Boxes indicate the minimal DUX4 binding sites. For decoy 3, mutated bases used to generate Decoy3-Mut are indicated by arrows.

Figure 2:
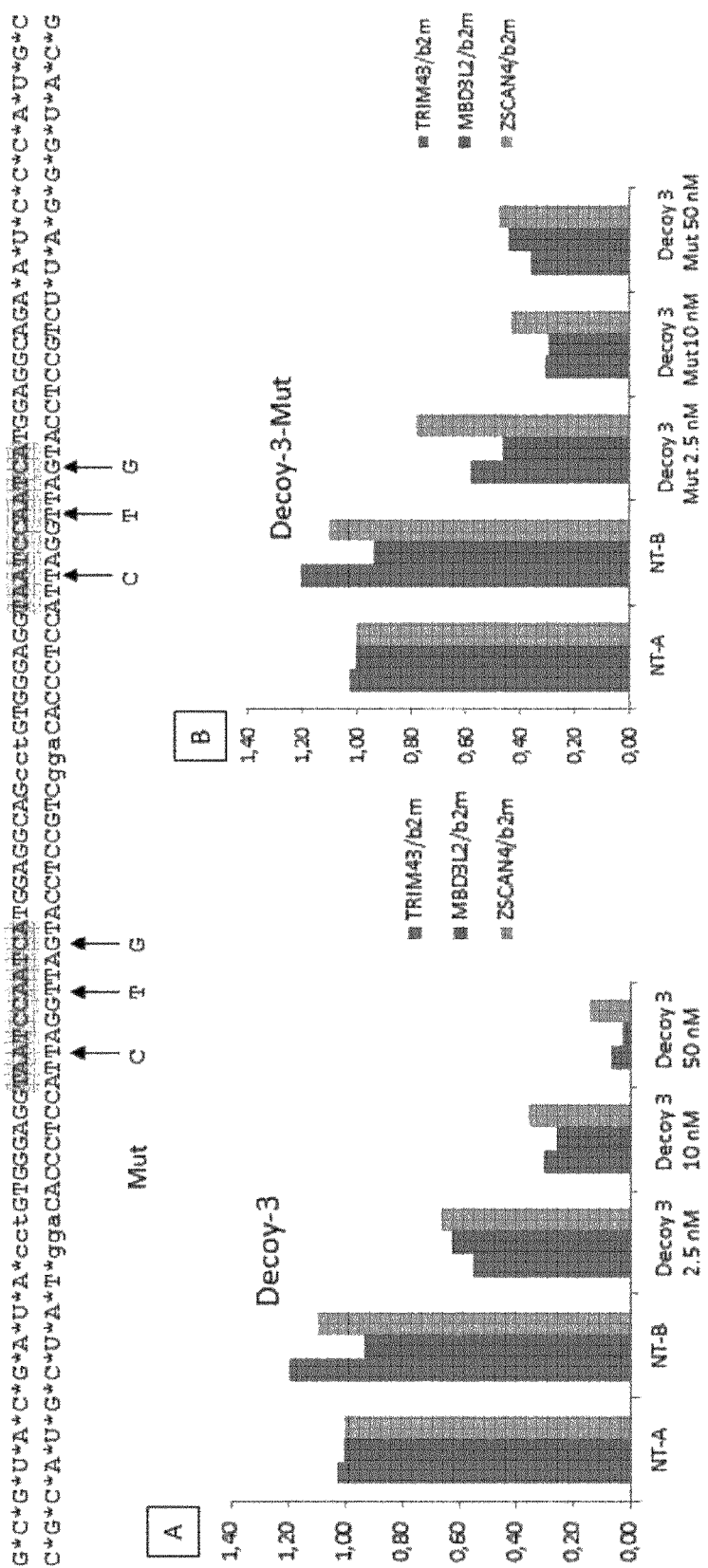
Figure 2:
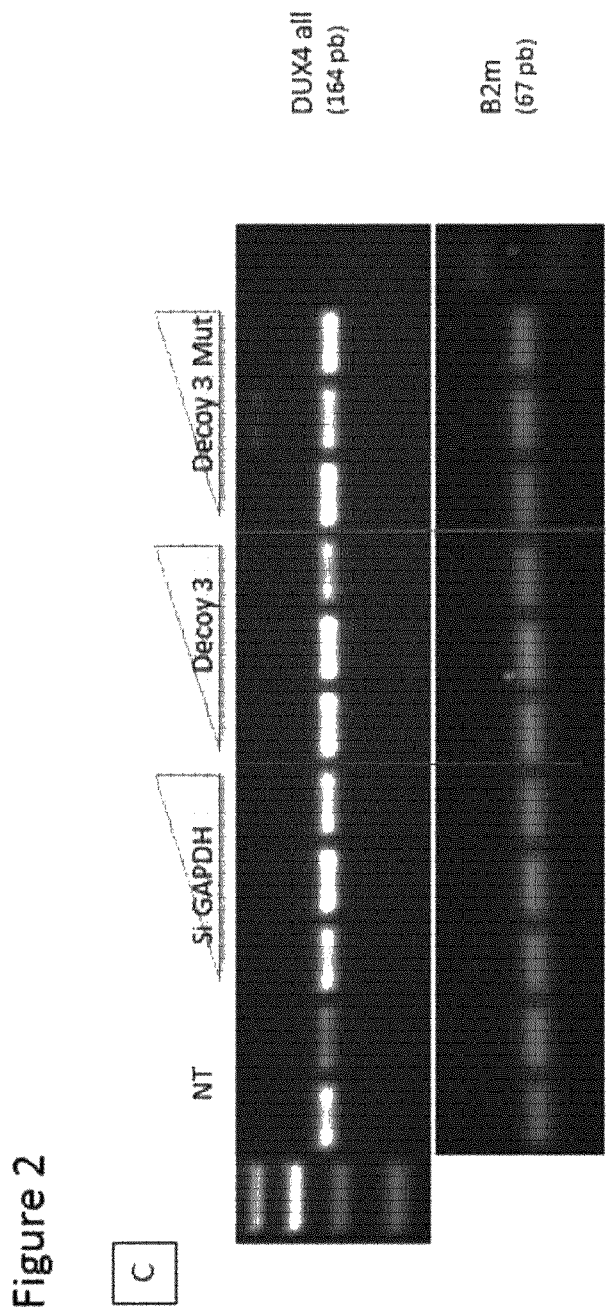

FIG. 2: DUX4-Decoy3 induces a down-regulation of the genes downstream of DUX4

The injected decoy (Decoy-3 (SEQ ID NO:19 & SEQ ID NO:34)) is represented. Arrows indicate the position of the mutated bases on upper strand introduced to create the Decoy-Mut. * represents 2'Omethyl modifications with phosphorothioate linkage. FSHD cells have been transfected in a dose dependent manner with either a DUX4-decoy (A) or mutated DUX4-decoy at day 2 of differentiation (B). 48 h post transfection, cells were harvested and total RNA extracted. RT was realized using a polydT oligonucleotides. A and B Expression levels of 3 genes downstream DUX4 was measured by qPCR. C: PCR allowing DUX4 mRNA detection was performed and run on an agarose gel (right). As expected, no modulation of DUX4 mRNA was observed since the decoy does not target mRNA. B2M was used as the reference gene.

Figure 3:
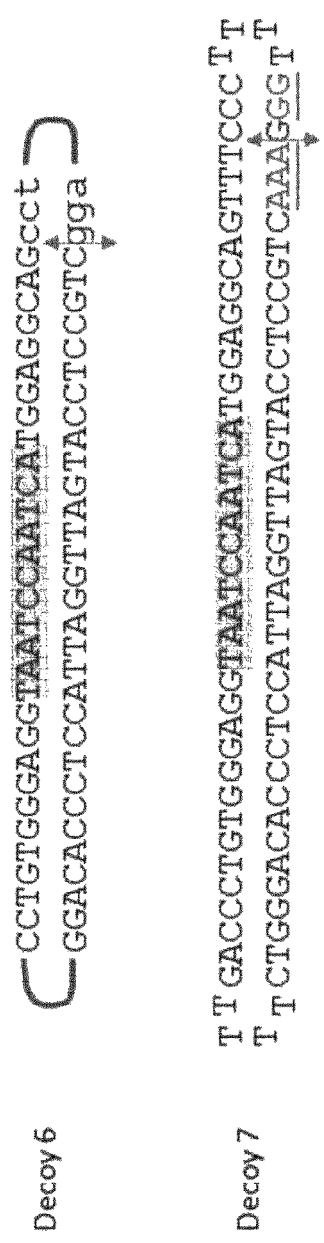
Figure 3:
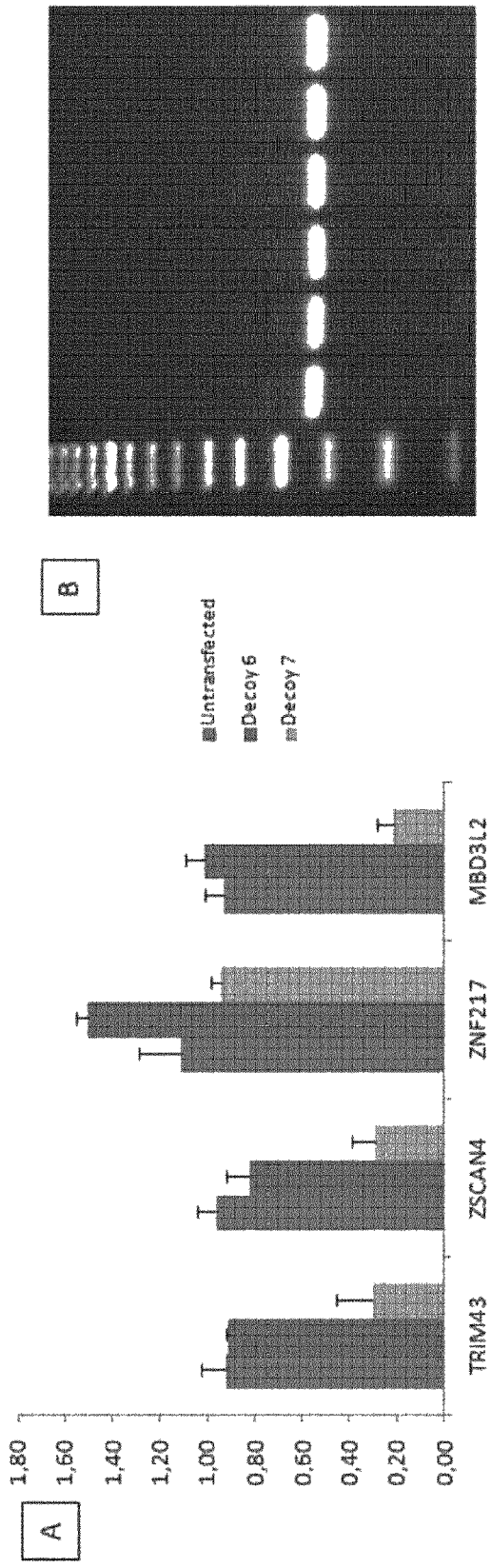

FIG. 3: DUX4 decoy7 induces a down-regulation of the genes downstream of DUX4

The injected decoy (Decoy-6 (SEQ ID NO:24); and Decoy-7 (SEQ ID NO:20)) is represented. The bases underlined carry phosphorothioate linkage. FSHD cells have been transfected with 1 µg of DNA. Four days after differentiation, cells were harvested and total RNA extracted. A: a RT-qPCR was performed to analyze the expression of 3 genes downstream DUX4 and 1 control gene (ZNF217). B: DUX4 expression was analyzed by PCR. B2M was used as the reference gene. The molecules are linear duplex DNAs with an interruption in the middle of one strand (arrow) The hexaethyleneglycol linkers are represented by gray brackets.

Figure 4:
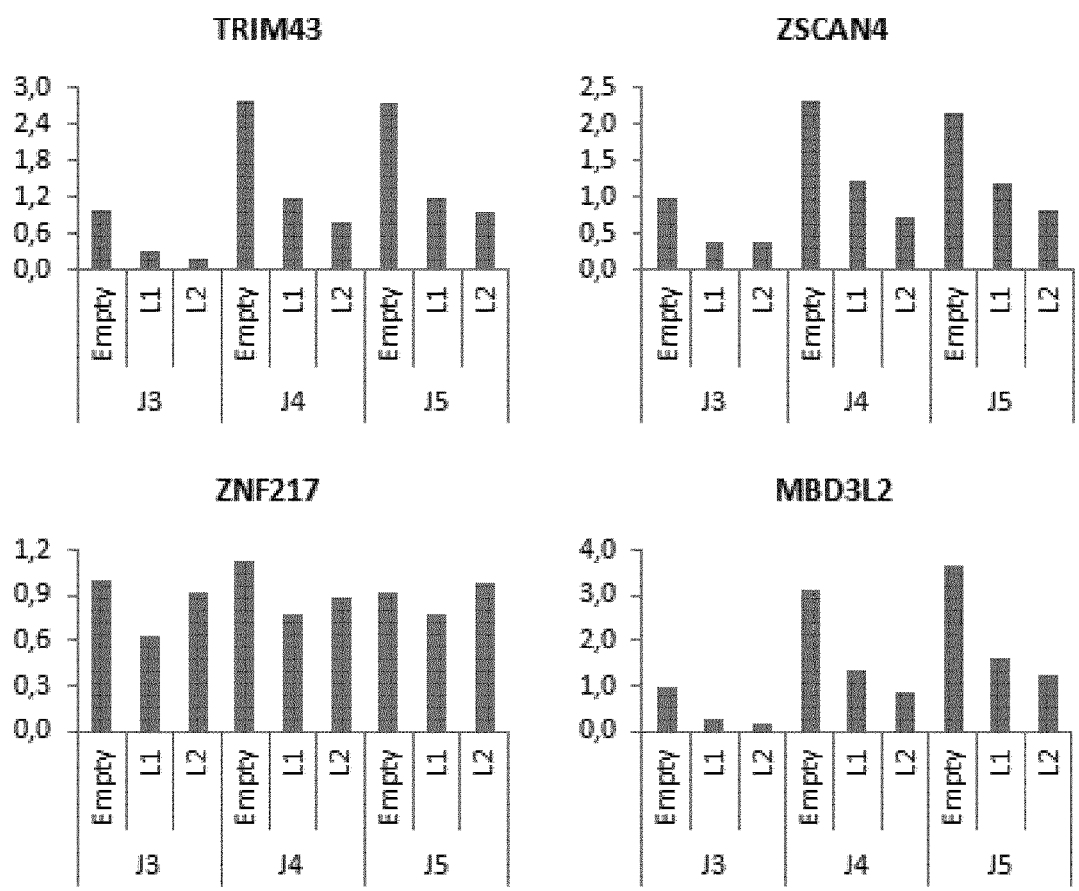

FIG. 4: Transduction of FSHD cells by a lentiviral vector carrying the DUX4-decoy induces a downregulation of the DUX4 footprint genes.

FSHD cells were transduced by an empty lentiviral vector or carrying either (i) 5 times the sequence (L1, SEQ ID NO: 21)
TCGAGAATAACCCAATCAAATTAATTTAATCATAATCCAATCAAGATAAT

TGAATCATGGTAATTGAATCAGGTAATTGAATCATGGTAATCCAATCAC or the sequence (L2, SEQ ID NO: 22)
TCGAGTAATTTAATCAGCGTACGATAATCCCATGCGTAATCCAATCAGCG

TACGATAATCCCATGCGTAATCCAATCAGCGTACGATAATCCCATGCGC.

Cells were harvested at day 3 and 4 after induction of differentiation. qPCR were performed to analyze expression of 3 genes downstream of DUX4. Expression of ZNF217 was used as a control. B2M was used as the reference gene.

Figure 5:
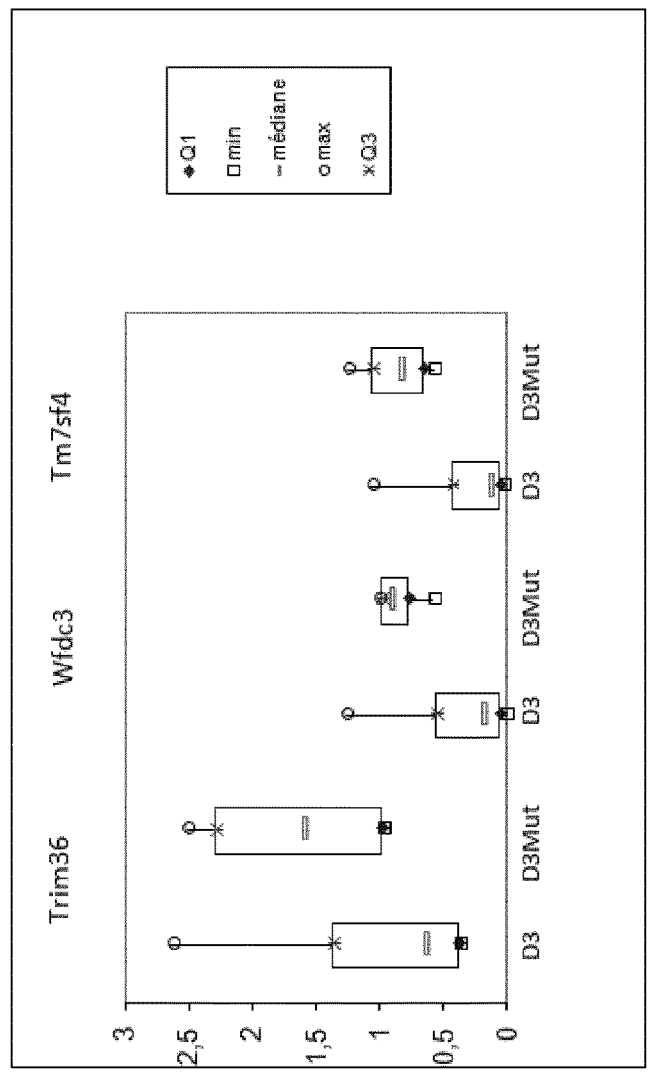

FIG. 5: Intramuscular injection of decoy 3 induces a downregulation of murine genes downstream of DUX4

C57bL6 mice were electroporated with both a DUX4 expression plasmid (pSC2) and either the Decoy3 (SEQ ID NO:19 & SEQ ID NO:34) or Decoy3-Mut. Five days later, mice were sacrificed and expression levels of 3 murine genes downstream of DUX4 were analyzed. The reference gene was Psma2.

Figure 6:
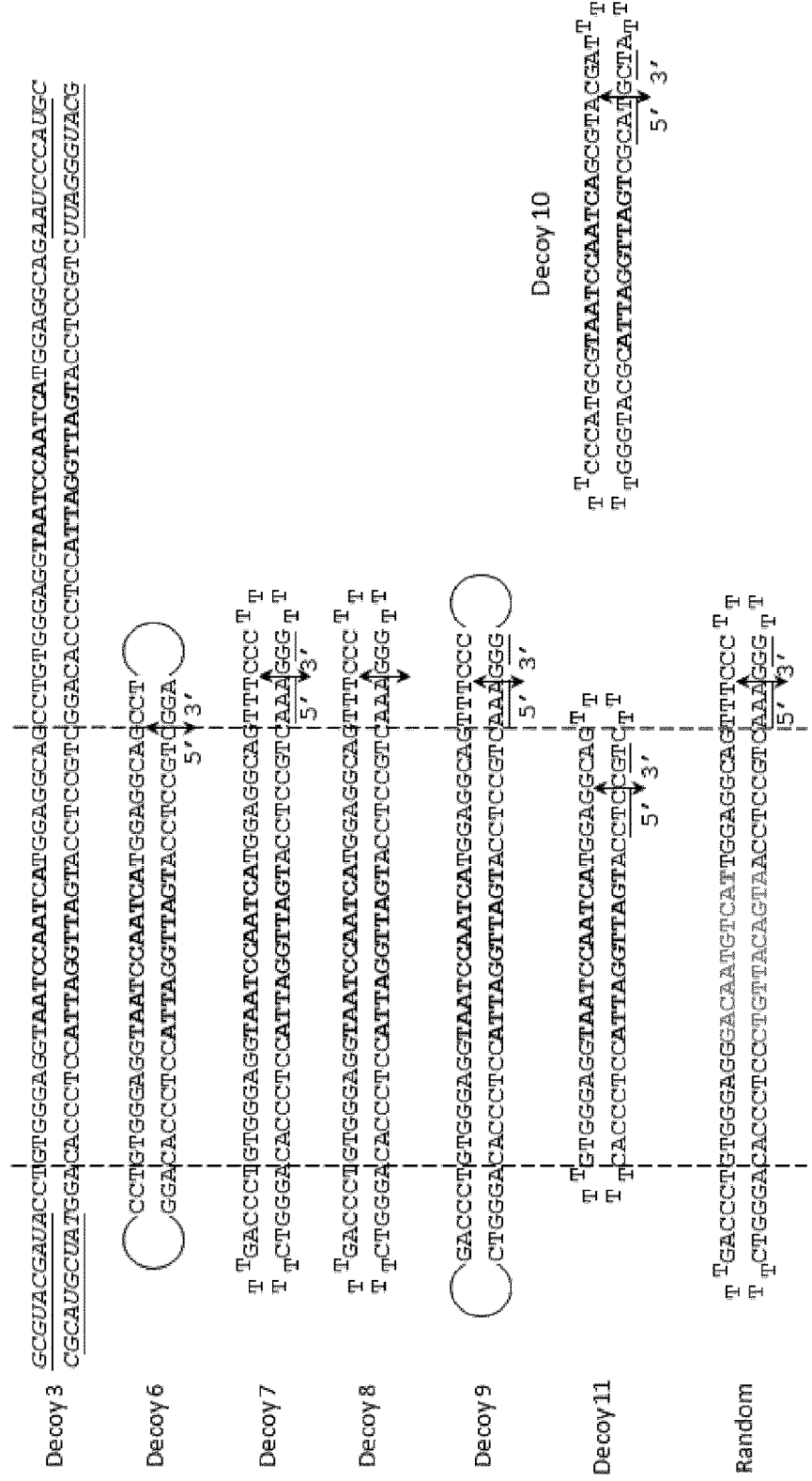

FIG. 6: further representative decoys

The decoys are double strand DNA synthetized either as one single DNA strand (decoys 6-11 (Decoy-6 (SEQ ID NO:24); Decoy-7 (SEQ ID NO:20); Decoy-8 (SEQ ID NO:20); Decoy-9 (SEQ ID NO:25); Decoy-10 (SEQ ID NO:27); and Decoy-11 (nt 4-68 of SEQ ID NO:26), where double arrows indicate the position of the 5' and 3' ends of the oligonucleotide) or as 2 oligonucleotides which are hybridized together (Decoy 3 (SEQ ID NO:19 & SEQ ID NO:34)). Chemical modifications are:

Italic: 2'Omethyl modifications.

Underlined: bases carrying phosphorothioate linkage

The hexaethyleneglycol linkers are represented in decoys 6 and 9 as circles. Bold nucleotides indicate the minimal DUX4 binding sites.

Figure 7:
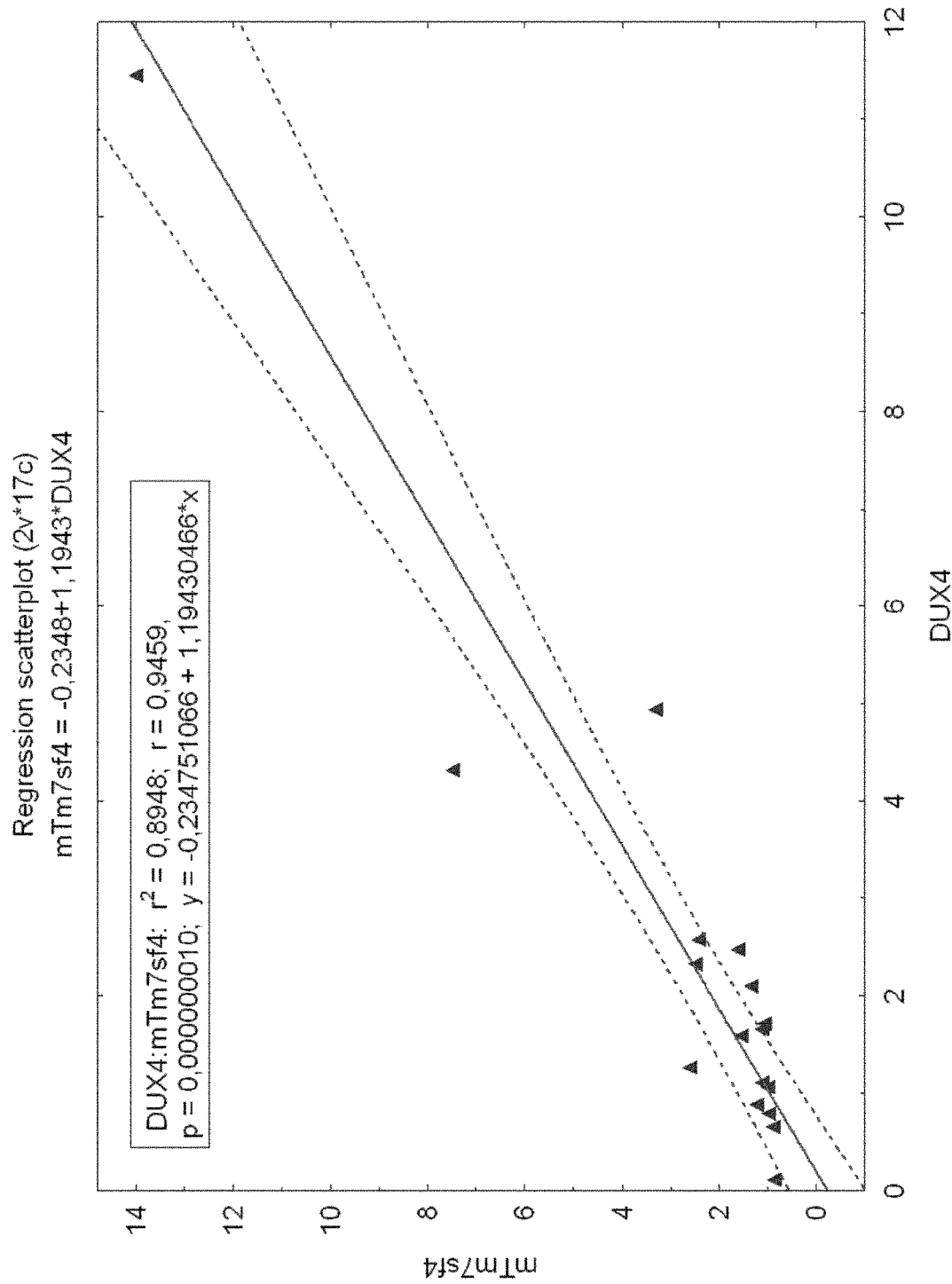

FIG. 7: mouse model validation

Tibialis anterior (TA) muscles were electrotransfered with pSC2 plasmid coding for DUX4. Expression levels of both DUX4 and Tm7sf4 were analyzed by pPCR. A multi parametric analysis of variance (MANOVA) and a Newman-Keuls post-hoc test was performed. A strong correlation between DUX4 and Tm7sf4 was observed (n=18 TA injected muscles; $R^2$=0.8948; p=10e-8).

Figure 8:
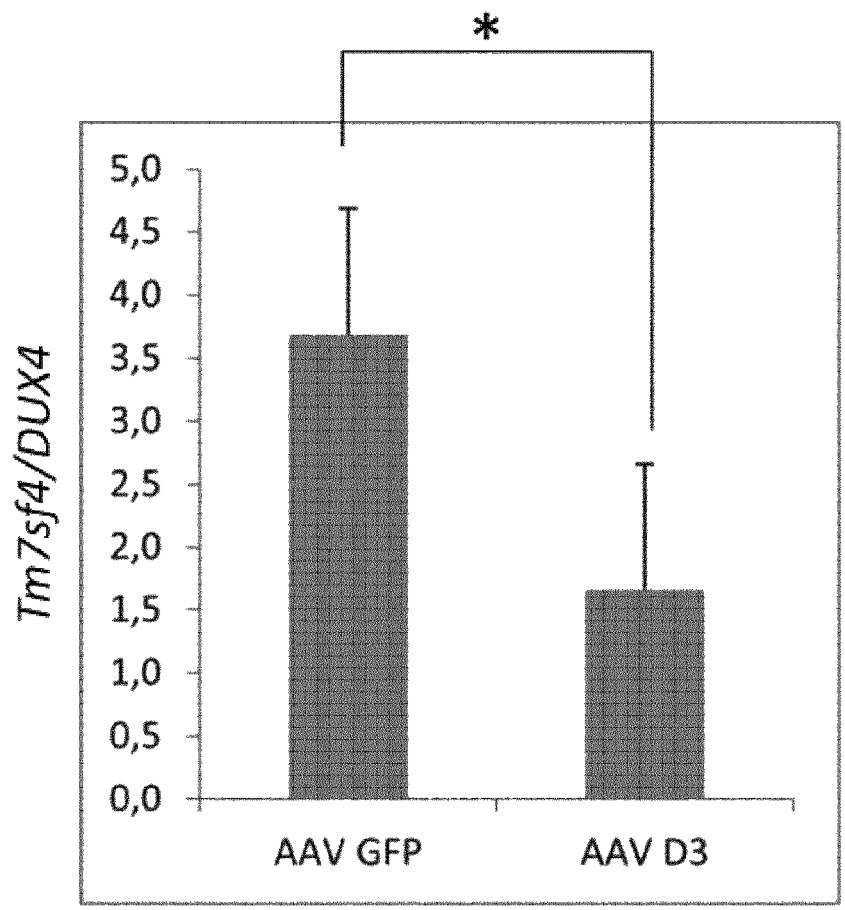

FIG. 8: Intramuscular injection of a viral vector producing a DUX4 decoy induces a downregulation of murine genes downstream of DUX4

Tibialis anterior muscles were first injected with either AAV D3 (n=8) or AAV GFP (n=8) (2,5 10e10 vg/TA). (Decoy: nucleotides 1-61 of SEQ ID NO:28) Two weeks later, TAs were electrotransfered with pCS2 plasmid. Expression levels of both DUX4 and Tm7sf4 were investigated by qPCR. *p<0.05 (T-test). All data represent mean+ standard deviation.

Figure 9:
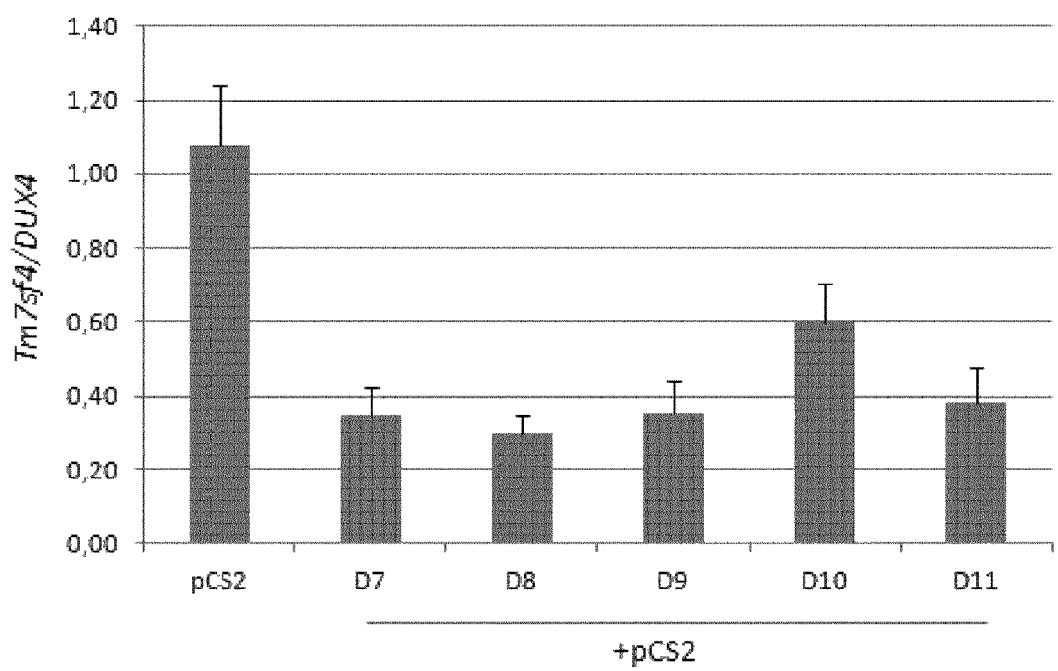

FIG. 9: Intramuscular injection of viral vectors producing different DUX4 decoys induces a downregulation of murine genes downstream of DUX4

TAs were electrotransfered with pCS2 alone (n=18) or pCS2+decoy (n=12 each). Expression levels of both DUX4 and Tm7sf4 were investigated by qPCR. All data represent mean+standard error of the mean.

Figure 10:
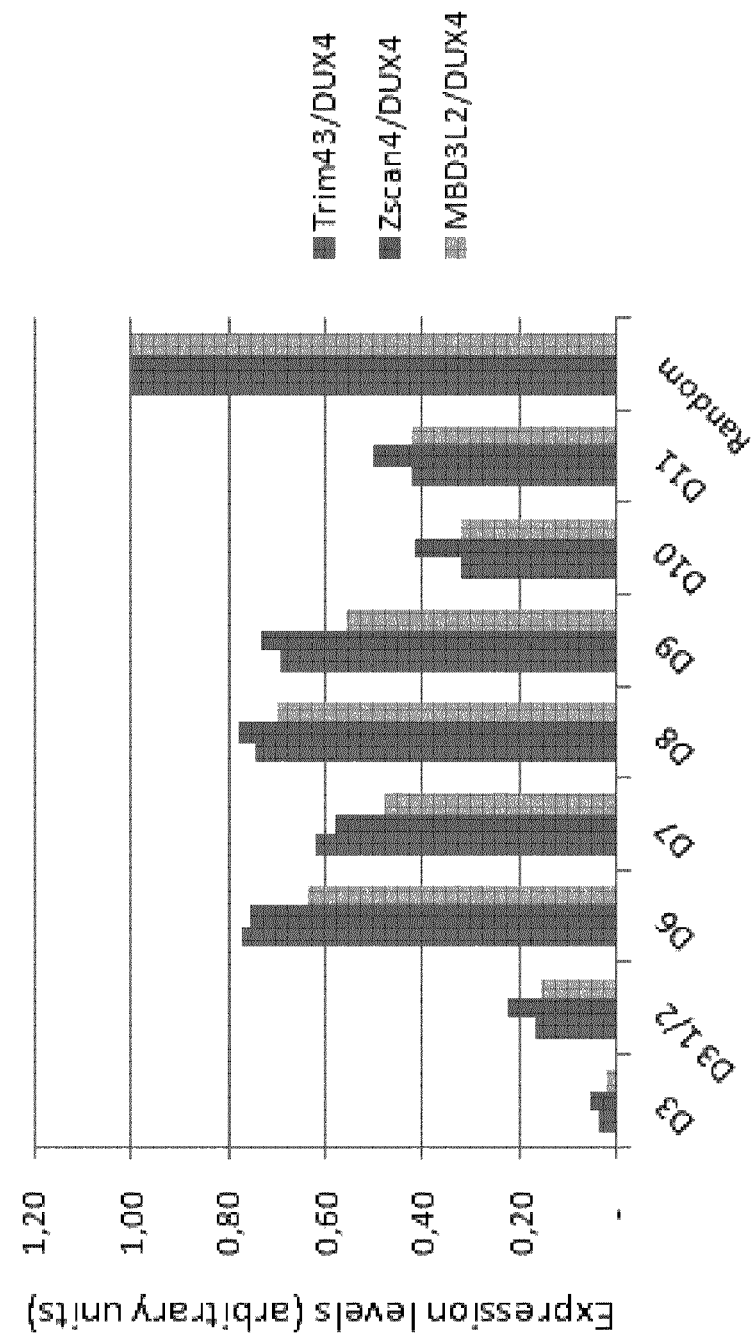

FIG. 10: DUX4 decoys induce a down-regulation of a gene downstream of DUX4

FSHD cells were transfected with different decoys. Cells were harvested at day 3 and 4 after induction of differentiation. qPCR were performed to analyze expression of 3 genes downstream of DUX4

EXAMPLES

Material and Methods
Decoy Preparation

The DNA sequences containing the putative DUX4 binding site (here after called decoy) were designed according to the DUX4-fl motif previously described (14). Four modified double strand oligonucleotides were synthetized:

```
Decoy-1
                                         (SEQ ID NO: 17)
(forw: G*A*G*GTAATCCAATCATG*G*A;

(SEQ ID NO: 32)
rev: U*C*C*ATGATTGGATTACC*U*C),
Decoy-2
                                         (SEQ ID NO: 18)
(Forw: U*G*CGTAATCCAATCAGCG*U.

(SEQ ID NO: 33)
Rev: A*C*GCTGATTGGATTACGC*A),
Decoy-3
                                         (SEQ ID NO: 19)
(Forw: G*C*G*U*A*C*G*A*U*A*cctGTGGGAGGTAATCCAATCAT GGAGGCAGcctGTGGGAGGTAATCCAATCATGGAGGCAGA*A*U*C*C

*A*U*G*C;

(SEQ ID NO: 34)
Rev: G*C*A*U*G*G*A*U*U*CTGCCTCCATGATTGGATTACCTCC

CACaggCTGCCTCCATGATTGGATTACCTCCCACaggU*A*U*C*G*U*A

*C*G*C),
and
Decoy 3-Mut
                                         (SEQ ID NO: 35)
(Forw: G*C*G*U*A*C*G*A*U*A*cctGTGGGAGGTACTCCTATGAT GGAGGCAGcctGTGGGAGGTACTCCTATGATGGAGGCAGA*A*U*C*C*C

*A*U*G*C;

(SEQ ID NO: 36)
Rev: G*C*A*U*G*G*A*U*U*CTGCCTCCATCATAGGAGTACCTCC

CACaggCTGCCTCCATCATAGGAGTACCTCCCACaggU*A*U*C*G*U*A

*C*G*C)
``` where * represents 2'OMethyl ribonucleotides with phosphorotioate links.

The three linear duplex DNAs with one hexaethyleneglycol linker at both ends mimicking double strand DNA were synthetized:

```
Decoy-4
                                         (SEQ ID NO: 29)
(TCCAATCATGGAGGCAG-CTGCCTCCATGATTGGATTACCTCCCAC-GT

GGGAGGTAA);

Decoy-5
                                         (SEQ ID NO: 30)
(TACGCTGATTGGATTACGCATGGG-CCCATGCGTAATCCAATCAGCGT

ACGAT-ATCG);

Decoy-6
                                         (SEQ ID NO: 24)
(CTGCCTCCATGATTGGATTACCTCCCACAGG-CCTGTGGGAGGTAATCC

AATCATGGAGGCAGCCT-AGG).
``` where - represents the hexaethyleneglycol linker.

Two linear duplexes mimicking double strand DNA were synthetized:

```
Decoy7:
                                         (SEQ ID NO: 20)
A*A*ACTGCCTCCATGATTGGATTACCTCCCACAGGGTCTTTTGACCCTG

TGGGAGGTAATCCAATCATGGAGGCAGTTTCCCTTTTG*G*G

Decoy7-Mut:
                                         (SEQ ID NO: 37)
A*A*A*CTGCCTCCATCATAGGAGTACCTCCCACAGGGTCTTTTGACCCT

GTGGGAGGTACTCCTATGATGGAGGCAGTTTCCCTTTTG*G*G
```

Further linear decoys mimicking double-stranded DNA were also synthesized and are represented in FIG. 6 (decoys 8 to 11)

Forward and reverse oligonucleotides for decoys 1, 2 and 3 were annealed at equimolar concentration in a final volume of 50 µl and heated at 95° C. for 4 min. For decoys 4 to 11, a 1 µg/µl solution was heated at 95° C. during 4 min. The ligation was performed with the T4 ligase according to the manufacturer protocol (Biolabs).

For the lentiviral constructs, the oligonucleotides for

```
Decoy L1
                                         (SEQ ID NO: 21)
(Forw: TCGAGAATAACCCAATCAAATTAATTTAATCATAATCCAATCA

AGATAATTGAATCATGGTAATTGAATCAGGTAATTGAATCATGGTAATCC

AATCAC;

(SEQ ID NO: 38)
Rev: TCGAGTGATTGGATTACCATGATTCAATTACCTGATTCAATTACC

ATGATTCAATTATCTTGATTGGATTATGATTAAATTAATTTGATTGGGTT

ATTC)
and

Decoy-L2
                                         (SEQ ID NO: 22)
(Forw: TCGAGTAATTTAATCAGCGTACGATAATCCCATGCGTAATCCA

ATCAGCGTACGATAATCCCATGCGTAATCCAATCAGCGTACGATAATCCC

ATGCGC;

(SEQ ID NO: 39)
Rev: TCGAGCGCATGGGATTATCGTACGCTGATTGGATTACGCATGGGA

TTATCGTACGCTGATTGGATTACGCATGGGATTATCGTACGCTGATTAAA

TTAC)
``` were annealed at equimolar concentration in a final volume of 50 µl and heated at 95° C. for 4 min and then cloned into pBlue Script using the XhoI restriction site, thus allowing concatemer formation. This shuttle vector was then digested by NotI and ApaI before to be cloned into pLL3.7 lentiviral vector digested by the same enzymes and previously modified to introduce a neomycine cassette by removing the GFP gene using the NheI and EcoRI restriction sites.

Transfection and Transduction

The cells used for the transfection are immortalized FSHD cells isolated from a mosaic patients and previously described (15). The clones were cultivated in proliferation medium [4 vols of DMEM, 1 vol of 199 medium, FBS 20%, gentamycin 50 mg/ml (Life technologies, Saint Aubin, France)] supplemented with insulin 5 mg/ml dexamethasone 0.2 mg/ml, b-FGF 0.5 ng/ml, hEGF 5 ng/ml and fetuine 25 mg/ml. Differentiation medium was composed of DMEM supplemented with insulin (10 mg/ml). Myoblasts were plated at 25000 cell/cm$^2$. Two days later, the proliferation medium was replaced by differentiation medium. The transfection was realized at day 2 of differentiation using lipofectamine RNAIMAX reagent according to the manufacturer protocol (Invitrogen) with a ratio of 1:5 between DNA and RNAIMAX. Cells were harvested 4 days after triggering differentiation.

The pLL3.7-Decoy vectors (L1 and L2) were produced in human embryonic kidney 293 cells by quadri-transfection of plasmids encoding gag-pol proteins, Rev protein, envelop proteins (VSVg) and the transgene using PEI. 48 and 72 h later; the viral vector is filtered (0.22 mm) before being directly used to transduce myoblasts. Transduced cells were selected during 15 days using G418 (0.5 µg/µl final concentration). The transduced cells were primary FSHD cells isolated from either a fetal quadriceps (16 weeks of development carrying 4 D4Z4 repeats) or and adult trapezius (25 years old carrying 4.4 D4Z4 repeats). Cells were then plated at 25000 cell/cm$^2$ and 2 days later, proliferation medium was replaced by differentiation medium. Cells were harvested at day 4 of differentiation.

In Vivo Experiments

Tibialis anterior (TA) of 6- to 8-week-old female C571316 mice were electrotransfered (Mode: LV; voltage: 200V/cm; P. length: 20 msec; Pulses: 8; Interval: 500 ms; Polarity: unipolar) with 2 µg of pCS2-mkgDUX4 expression plasmid (Addgene #21156) and 10 µg of either Decoy-3 or Decoy-3-Mut in a final volume of 40 µl. Five days after electrontransfer, mice were sacrificed and TA muscles were frozen in liquid nitrogen. RNAs were extracted using the FastPrep kit (MP biomedicals) according to manufacturer instructions.

RNA Extraction and PCR

Trizol was directly added on either cells or mouse muscles and RNA extraction was performed according to the manufacturer protocol (Life technologies, Saint Aubin, France). RNA concentration was determined using a nanodropND-1000 spectrophotometer (Thermo Scientific, Wilmington, USA). The RT was carried out on 1 µg of total RNA with Roche Transcriptor First Strand cDNA Synthesis Kit (Roche, Meylan, France) at 50° C. for 60 min with 1 µl of oligo dT in a final volume of 10 µl. Quantitative PCRs were performed in a final volume of 9 ml with 0.4 µl of RT product, 0.18 µl of each forward and reverse primers 20 pmol/µl (Table 1), and 4.5 µl of SYBR Green mastermix 2× (Roche, Meylan, France). The qPCR was run in triplicates on a LightCycler 480 Real-Time PCR System (Roche, Meylan, France). The qPCR cycling conditions were 94° C. for 5 min, followed by 50 cycles at 95° C. for 30 s and 60° C. for 15 s and 72° C. for 15 s. The PCR for DUX4 were performed as previously described (16). B2M was used a normalized.

AAV Transduction Experiments:

For the AAV constructs (pAAV-decoy), the oligonucleotides Forward (CCTGTGGGAGGTAATCCAATCATG-GAGGCAGCCTGTGGGAGGTAATCCAATCA TGGAG-GCAG (SEQ ID NO:28)) and reverse (CTGCCTCCATGATTGGATTACCTCCCACAGGCTGC-CTCCATGATTGGATTACCT CCCACAGG (SEQ ID NO:40)) were annealed at equimolar concentration in a final volume of 20 µl and heated at 95° C. for 4 min and then cloned into pGG2 plasmid which was previously digested by XbaI and HpaI restriction enzymes (blunted using klenow).

AAV vectors were produced in human embryonic kidney 293 cells by triple-transfection method using the calcium phosphate precipitation technique with the pAAV-decoy plasmid, the pXX6 plasmid coding for the adenoviral sequences essential for AAV production, and the pRepCAp plasmid coding for AAV-1 capsid. The virus is then purified by one cycle of iodixanol gradient and washed and concentrated using Am icon Ultra column. The final viral preparations were kept in PBS solution at −80° C. The particle titer (number of viral genomes) was determined by quantitative PCR. The injections of TA were performed on 6-8 week-old female C571316 mice with 2.5.10e$^{10}$ AAV viral genomes.

Results

In Vitro Experiments—Use of Oligonucleotide Decoys

Figure 1:
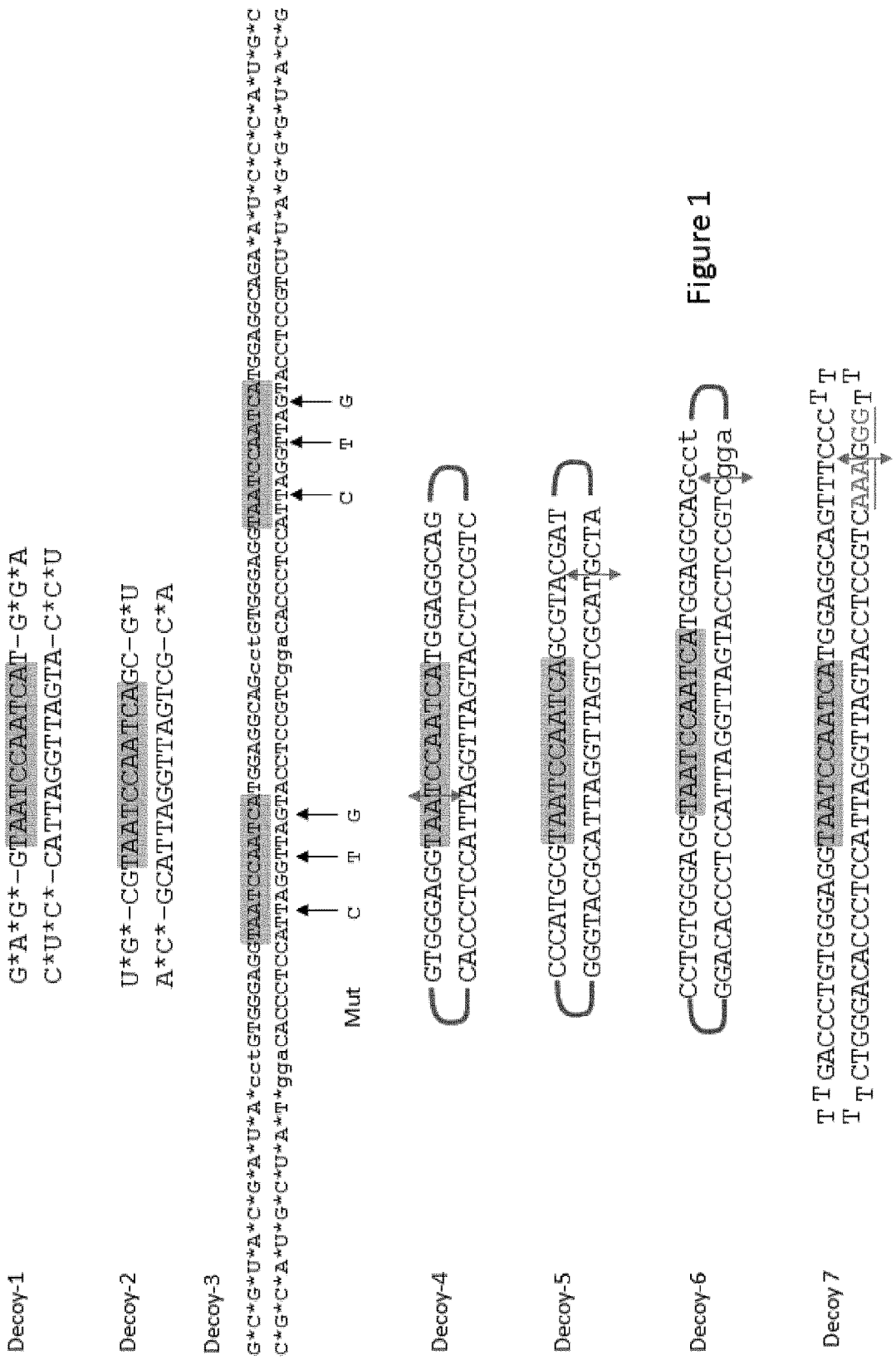
FIG. 1: representative decoys

In order to select the most efficient trap for DUX4, several decoys were designed according to the DUX4-fl motif previously described (14). In this article, the authors have identified 2 motifs, TAAYYBAATCA (SEQ ID NO:1) and TAAYBYAATCA (SEQ ID NO:2) (according to DNA IUB Code), respectively corresponding to MaLR-associated sites and sites not associated with repeats, leading to 18 possible sequences. We selected 1 of them: TAATCCAATCA (SEQ ID NO:5) to design our decoys. we designed several decoys (FIG. 1) and transfected them in immortalized FSHD cells. Decoy-1, -2, -4, -5 and -6 induced only a moderate modification of the expression of the genes downstream of DUX4. However, a strong decrease of TRIM43, MBD3L2 and ZSCAN4 expression was observed in a dose dependent manner in presence of either Decoy-3 (FIG. 2A) or Decoy 7 (FIG. 3A). As a control, when Decoy-3-Mut (carrying the same sequence as decoy-3 but 3 nucleotides were mutated in the DUX4-fl motif) was transfected, the decrease was much less important (FIGS. 2 and 3).

DUX4 expression level was next examined in the transfected cells. Since the decoys trap DUX4, no variation in DUX4 mRNA was expected. As shown in FIG. 2C, the transfection of either decoy-3 or decoy-3-Mut did not induce a modification of DUX4 expression. Similar results were obtained with decoy 7 (FIG. 3B).

In Vitro Experiments—Use of Viral Vectors

One decoy was also vectorized and decoy-L1 and L2 were introduced into the FSHD myoblasts using a lentiviral vector. The presence of either decoys L1 or L2 in these cells induced a downexpression of the genes downstream of DUX4 (TRIM43, MBD3L2, DEFB103 and ZSCAN4) but no down-regulation of ZNF217 was observed (as expected, ZNF217 is not one of the DUX4 "footprint" genes). This experiment was performed 3 times (FIG. 4).

In Vivo Experiments

The capability of decoy-3 to trap DUX4 was also investigated in vivo. We co-transfected a DUX4 expression plasmid and the Decoy-3 or Decoy-3-Mut in the tibialis anterior (TA) of 6- to 8-week-old female C571316 mice. As shown in FIG. 5, while Decoy-3-Mut was not able to inhibit the expression of the genes downstream of DUX4, with Decoy-3, the expression of these genes was reduced 2.5 to 6 fold.

In Vivo Experiments—Further Validation of the Approach

In vivo experiments were further conducted (FIGS. 7-9) to confirm the potent effect of the decoys of the invention.

First, the correlation between DUX4 expression and a DUX4 target gene (mTm7sf4) was verified in mouse TA muscles, after electrotransfert of the pSC2 plasmid coding for DUX4. FIG. 7 shows a strict correlation between DUX4 expression and mTm7sf4 expression. Accordingly, this target gene was used for determining the effect of the decoys of the invention in vivo.

Then, AAV vectors carrying in their genome two DUX4 binding sites as represented in FIG. 8 were produced and injected in TA muscles of mice also receiving via electrontransfer a DUX4-coding plasmid. The results show that the AAV carrying the decoy oligonucleotide (AAV D3) significantly decreases mTm7sf4 expression as compared to a control AAV carrying GFP, thereby showing that efficient DUX4 inhibition can be achieved in vivo via viral decoy transfer.

The decoy oligonucleotides were also directly electrotransfered into the TA muscles of mice in the presence of a DUX4-coding plasmid (FIG. 9). The results show a strong decrease of Tm7sf4 expression in the presence of the decoys compared to the electrotransfert of the DUX4-coding plasmid alone, showing that oligonucleotide decoys of different sequences also achieved efficient DUX4 inhibition in vivo.

FIG. 10 shows that transfecting oligonucleotide decoys of different sequences leads to a decreased expression of 3 genes downstream of DUX4.

Altogether, these data show that DUX4 decoys are powerful tools for achieving DUX4 target genes repression. Therefore, these decoys, whether administered as oligonucleotides or as part of a viral genome, represent invaluable tools for the treatment of FSHD.

REFERENCES 1. van der Maarel, S. M., Miller, D. G., Tawil, R., Filippova, G. N. and Tapscott, S. J. (2012) Facioscapulohumeral muscular dystrophy: consequences of chromatin relaxation. *Curr Opin Neurol,* 25, 614-620.
2. van Deutekom, J. C., Wijmenga, C., van Tienhoven, E. A., Gruter, A. M., Hewitt, J. E., Padberg, G. W., van Ommen, G. J., Hofker, M. H. and Frants, R. R. (1993) FSHD associated DNA rearrangements are due to deletions of integral copies of a 3.2 kb tandemly repeated unit. *Human molecular genetics,* 2, 2037-2042.
3. Lunt, P. W., Noades, J. G., Upadhyaya, M., Sarfarazi, M. and Harper, P. S. (1988) Evidence against location of the gene for facioscapulohumeral muscular dystrophy on the distal long arm of chromosome 14. *J Neurol Sci,* 88, 287-292.
4. Lemmers, R. J., Tawil, R., Petek, L. M., Balog, J., Block, G. J., Santen, G. W., Amell, A. M., van der Vliet, P. J., Almomani, R., Straasheijm, K. R. et al. (2012) Digenic inheritance of an SMCHD1 mutation and an FSHD-permissive D4Z4 allele causes facioscapulohumeral muscular dystrophy type 2. *Nature genetics,* 44, 1370-1374.
5. Lemmers, R. J., van der Vliet, P. J., Klooster, R., Sacconi, S., Camano, P., Dauwerse, J. G., Snider, L., Straasheijm, K. R., van Ommen, G. J., Padberg, G. W. et al. (2010) A unifying genetic model for facioscapulohumeral muscular dystrophy. *Science,* 329, 1650-1653.
6. Lemmers, R. J., van der Vliet, P. J., van der Gaag, K. J., Zuniga, S., Frants, R. R., de Knijff, P. and van der Maarel, S. M. (2010) Worldwide population analysis of the 4q and 10q subtelomeres identifies only four discrete interchromosomal sequence transfers in human evolution. *Am J Hum Genet,* 86, 364-377.
7. Lemmers, R. J., Wohlgemuth, M., van der Gaag, K. J., van der Vliet, P. J., van Teijlingen, C. M., de Knijff, P., Padberg, G. W., Frants, R. R. and van der Maarel, S. M. (2007) Specific sequence variations within the 4q35 region are associated with facioscapulohumeral muscular dystrophy. *Am J Hum Genet,* 81, 884-894.
8. Scionti, I., Greco, F., Ricci, G., Govi, M., Arashiro, P., Vercelli, L., Berardinelli, A., Angelini, C., Antonini, G., Cao, M. et al. (2012) Large-scale population analysis challenges the current criteria for the molecular diagnosis of fascioscapulohumeral muscular dystrophy. *Am J Hum Genet,* 90, 628-635.
9. Thomas, N. S., Wiseman, K., Spurlock, G., MacDonald, M., Ustek, D. and Upadhyaya, M. (2007) A large patient study confirming that facioscapulohumeral muscular dystrophy (FSHD) disease expression is almost exclusively associated with an FSHD locus located on a 4qA-defined 4qter subtelomere. *J Med Genet,* 44, 215-218.
10. Gabriels, J., Beckers, M. C., Ding, H., De Vriese, A., Plaisance, S., van der Maarel, S. M., Padberg, G. W., Frants, R. R., Hewitt, J. E., Collen, D. et al. (1999) Nucleotide sequence of the partially deleted D4Z4 locus in a patient with FSHD identifies a putative gene within each 3.3 kb element. *Gene,* 236, 25-32.
11. Dixit, M., Ansseau, E., Tassin, A., Winokur, S., Shi, R., Qian, H., Sauvage, S., Matteotti, C., van Acker, A. M., Leo, O. et al. (2007) DUX4, a candidate gene of facioscapulohumeral muscular dystrophy, encodes a transcriptional activator of PITX1. *Proc Natl Acad Sci USA,* 104, 18157-18162.
12. Yao, Z., Snider, L., Balog, J., Lemmers, R. J., Van Der Maarel, S. M., Tawil, R. and Tapscott, S. J. (2014) DUX4-induced gene expression is the major molecular signature in FSHD skeletal muscle. *Human molecular genetics.*
13. Ferreboeuf, M., Mariot, V., Furling, D., Butler-Browne, G., Mouly, V. and Dumonceaux, J. (2014) Nuclear protein spreading: implication for pathophysiology of neuromuscular diseases. *Human molecular genetics.*
14. Geng, L. N., Yao, Z., Snider, L., Fong, A. P., Cech, J. N., Young, J. M., van der Maarel, S. M., Ruzzo, W. L., Gentleman, R. C., Tawil, R. et al. (2012) DUX4 Activates Germline Genes, Retroelements, and Immune Mediators: Implications for Facioscapulohumeral Dystrophy. *Dev Cell,* 22, 38-51.
15. Krom, Y. D., Dumonceaux, J., Mamchaoui, K., den Hamer, B., Mariot, V., Negroni, E., Geng, L. N., Martin, N., Tawil, R., Tapscott, S. J. et al. (2012) Generation of isogenic D4Z4 contracted and noncontracted immortal muscle cell clones from a mosaic patient: a cellular model for FSHD. *The American journal of pathology,* 181, 1387-1401.
16. Ferreboeuf, M., Mariot, V., Bessieres, B., Vasiljevic, A., Attie-Bitach, T., Collardeau, S., Morere, J., Roche, S., Magdinier, F., Robin-Ducellier, J. et al. (2014) DUX4 and DUX4 downstream target genes are expressed in fetal FSHD muscles. *Human molecular genetics,* 23, 171-181.

SEQUENCE LISTING

<160> NUMBER OF SEQ ID NOS: 40

<210> SEQ ID NO 1
<211> LENGTH: 11
<212> TYPE: DNA
<213> ORGANISM: artificial
<220> FEATURE:
<223> OTHER INFORMATION: consensus

<400> SEQUENCE: 1
taayybaatc a                                                              11

<210> SEQ ID NO 2
<211> LENGTH: 11
<212> TYPE: DNA
<213> ORGANISM: artificial
<220> FEATURE:
<223> OTHER INFORMATION: consensus

<400> SEQUENCE: 2
taaybyaatc a                                                              11

<210> SEQ ID NO 3
<211> LENGTH: 11
<212> TYPE: DNA
<213> ORGANISM: artificial
<220> FEATURE:
<223> OTHER INFORMATION: binding site

<400> SEQUENCE: 3
taacccaatc a                                                              11

<210> SEQ ID NO 4
<211> LENGTH: 11
<212> TYPE: DNA
<213> ORGANISM: artificial
<220> FEATURE:
<223> OTHER INFORMATION: binding site

<400> SEQUENCE: 4
taatttaatc a                                                              11

<210> SEQ ID NO 5
<211> LENGTH: 11
<212> TYPE: DNA
<213> ORGANISM: artificial
<220> FEATURE:
<223> OTHER INFORMATION: binding site

<400> SEQUENCE: 5
taatccaatc a                                                              11

<210> SEQ ID NO 6
<211> LENGTH: 11
<212> TYPE: DNA
<213> ORGANISM: artificial
<220> FEATURE:
<223> OTHER INFORMATION: binding site

<400> SEQUENCE: 6
taattgaatc a                                                              11

<210> SEQ ID NO 7
<211> LENGTH: 13
<212> TYPE: DNA
<213> ORGANISM: artificial

```
<220> FEATURE:
<223> OTHER INFORMATION: decoy

<400> SEQUENCE: 7
gtaatccaat cat                                                        13

<210> SEQ ID NO 8
<211> LENGTH: 19
<212> TYPE: DNA
<213> ORGANISM: artificial
<220> FEATURE:
<223> OTHER INFORMATION: decoy

<400> SEQUENCE: 8
gaggtaatcc aatcatgga                                                  19

<210> SEQ ID NO 9
<211> LENGTH: 15
<212> TYPE: DNA
<213> ORGANISM: artificial
<220> FEATURE:
<223> OTHER INFORMATION: decoy

<400> SEQUENCE: 9
cgtaatccaa tcagc                                                      15

<210> SEQ ID NO 10
<211> LENGTH: 19
<212> TYPE: DNA
<213> ORGANISM: artificial
<220> FEATURE:
<223> OTHER INFORMATION: decoy

<400> SEQUENCE: 10
tgcgtaatcc aatcagcgt                                                  19

<210> SEQ ID NO 11
<211> LENGTH: 63
<212> TYPE: DNA
<213> ORGANISM: artificial
<220> FEATURE:
<223> OTHER INFORMATION: decoy

<400> SEQUENCE: 11
cctgtgggag gtaatccaat catggaggca gcctgtggga ggtaatccaa tcatggaggc     60
aga                                                                   63

<210> SEQ ID NO 12
<211> LENGTH: 82
<212> TYPE: DNA
<213> ORGANISM: artificial
<220> FEATURE:
<223> OTHER INFORMATION: decoy

<400> SEQUENCE: 12
gcguacgaua cctgtgggag gtaatccaat catggaggca gcctgtggga ggtaatccaa     60
tcatggaggc agaaucccau gc                                              82

<210> SEQ ID NO 13
<211> LENGTH: 28
<212> TYPE: DNA
<213> ORGANISM: artificial
<220> FEATURE:
<223> OTHER INFORMATION: decoy
```

```
<400> SEQUENCE: 13
gtgggaggta atccaatcat ggaggcag                                              28

<210> SEQ ID NO 14
<211> LENGTH: 28
<212> TYPE: DNA
<213> ORGANISM: artificial
<220> FEATURE:
<223> OTHER INFORMATION: decoy

<400> SEQUENCE: 14
cccatgcgta atccaatcag cgtacgat                                              28

<210> SEQ ID NO 15
<211> LENGTH: 34
<212> TYPE: DNA
<213> ORGANISM: artificial
<220> FEATURE:
<223> OTHER INFORMATION: decoy

<400> SEQUENCE: 15
cctgtgggag gtaatccaat catggaggca gcct                                       34

<210> SEQ ID NO 16
<211> LENGTH: 40
<212> TYPE: DNA
<213> ORGANISM: artificial
<220> FEATURE:
<223> OTHER INFORMATION: decoy

<400> SEQUENCE: 16
gaccctgtgg gaggtaatcc aatcatggag gcagtttccc                                 40

<210> SEQ ID NO 17
<211> LENGTH: 19
<212> TYPE: DNA
<213> ORGANISM: artificial
<220> FEATURE:
<223> OTHER INFORMATION: decoy

<400> SEQUENCE: 17
gaggtaatcc aatcatgga                                                        19

<210> SEQ ID NO 18
<211> LENGTH: 19
<212> TYPE: DNA
<213> ORGANISM: artificial
<220> FEATURE:
<223> OTHER INFORMATION: decoy

<400> SEQUENCE: 18
ugcgtaatcc aatcagcgu                                                        19

<210> SEQ ID NO 19
<211> LENGTH: 82
<212> TYPE: DNA
<213> ORGANISM: artificial
<220> FEATURE:
<223> OTHER INFORMATION: decoy

<400> SEQUENCE: 19
gcguacgaua cctgtgggag gtaatccaat catggaggca gcctgtggga ggtaatccaa           60
tcatggaggc agaaucccau gc                                                    82
```

```
<210> SEQ ID NO 20
<211> LENGTH: 88
<212> TYPE: DNA
<213> ORGANISM: artificial
<220> FEATURE:
<223> OTHER INFORMATION: decoy

<400> SEQUENCE: 20
aaactgcctc catgattgga ttacctccca cagggtcttt tgaccctgtg ggaggtaatc      60
caatcatgga ggcagtttcc cttttggg                                        88

<210> SEQ ID NO 21
<211> LENGTH: 99
<212> TYPE: DNA
<213> ORGANISM: artificial
<220> FEATURE:
<223> OTHER INFORMATION: decoy

<400> SEQUENCE: 21
tcgagaataa cccaatcaaa ttaatttaat cataatccaa tcaagataat tgaatcatgg      60
taattgaatc aggtaattga atcatggtaa tccaatcac                             99

<210> SEQ ID NO 22
<211> LENGTH: 99
<212> TYPE: DNA
<213> ORGANISM: artificial
<220> FEATURE:
<223> OTHER INFORMATION: decoy

<400> SEQUENCE: 22
tcgagtaatt taatcagcgt acgataatcc catgcgtaat ccaatcagcg tacgataatc      60
ccatgcgtaa tccaatcagc gtacgataat cccatgcgc                             99

<210> SEQ ID NO 23
<211> LENGTH: 28
<212> TYPE: DNA
<213> ORGANISM: artificial
<220> FEATURE:
<223> OTHER INFORMATION: decoy

<400> SEQUENCE: 23
cccatgcgta atccaatcag cgtacgat                                        28

<210> SEQ ID NO 24
<211> LENGTH: 68
<212> TYPE: DNA
<213> ORGANISM: artificial
<220> FEATURE:
<223> OTHER INFORMATION: decoy
<220> FEATURE:
<221> NAME/KEY: misc_feature
<222> LOCATION: (31)..(32)
<223> OTHER INFORMATION: hexaethylene linker between positions 31 and 32
<220> FEATURE:
<221> NAME/KEY: misc_feature
<222> LOCATION: (65)..(66)
<223> OTHER INFORMATION: hexaethylene linker between positions 65 and 66

<400> SEQUENCE: 24
ctgcctccat gattggatta cctcccacag gcctgtggga ggtaatccaa tcatggaggc      60
agcctagg                                                              68

<210> SEQ ID NO 25
<211> LENGTH: 80
<212> TYPE: DNA
```

```
<213> ORGANISM: artificial
<220> FEATURE:
<223> OTHER INFORMATION: decoy
<220> FEATURE:
<221> NAME/KEY: misc_feature
<222> LOCATION: (37)..(38)
<223> OTHER INFORMATION: hexaethylene linker between positions 37 and 38
<220> FEATURE:
<221> NAME/KEY: misc_feature
<222> LOCATION: (77)..(78)
<223> OTHER INFORMATION: hexaethylene linker between positions 77 and 78

<400> SEQUENCE: 25
aaactgcctc catgattgga ttacctccca cagggtcgac cctgtgggag gtaatccaat      60
catggaggca gtttcccggg                                                  80

<210> SEQ ID NO 26
<211> LENGTH: 68
<212> TYPE: DNA
<213> ORGANISM: artificial
<220> FEATURE:
<223> OTHER INFORMATION: decoy

<400> SEQUENCE: 26
ctgcctccat gattggatta cctcccactt tgtgggagg taatccaatc atggaggcag       60
ttttctgc                                                               68

<210> SEQ ID NO 27
<211> LENGTH: 64
<212> TYPE: DNA
<213> ORGANISM: artificial
<220> FEATURE:
<223> OTHER INFORMATION: decoy

<400> SEQUENCE: 27
tacgctgatt ggattacgca tgggttttcc catgcgtaat ccaatcagcg tacgattttt      60
atcg                                                                   64

<210> SEQ ID NO 28
<211> LENGTH: 62
<212> TYPE: DNA
<213> ORGANISM: artificial
<220> FEATURE:
<223> OTHER INFORMATION: decoy

<400> SEQUENCE: 28
cctgtgggag gtaatccaat catggaggca gcctgtggga ggtaatccaa tcatggaggc      60
ag                                                                     62

<210> SEQ ID NO 29
<211> LENGTH: 56
<212> TYPE: DNA
<213> ORGANISM: artificial
<220> FEATURE:
<223> OTHER INFORMATION: decoy 4
<220> FEATURE:
<221> NAME/KEY: misc_feature
<222> LOCATION: (17)..(18)
<223> OTHER INFORMATION: hexaethylene linker between positions 17 and 18
<220> FEATURE:
<221> NAME/KEY: misc_feature
<222> LOCATION: (45)..(46)
<223> OTHER INFORMATION: hexaethylene linker between positions 45 and 46

<400> SEQUENCE: 29
tccaatcatg gaggcagctg cctccatgat tggattacct cccacgtggg aggtaa         56
```

```
<210> SEQ ID NO 30
<211> LENGTH: 56
<212> TYPE: DNA
<213> ORGANISM: artificial
<220> FEATURE:
<223> OTHER INFORMATION: decoy 5
<220> FEATURE:
<221> NAME/KEY: misc_feature
<222> LOCATION: (24)..(25)
<223> OTHER INFORMATION: hexaethylene linker between positions 24 and 25
<220> FEATURE:
<221> NAME/KEY: misc_feature
<222> LOCATION: (52)..(53)
<223> OTHER INFORMATION: hexaethylene linker between positions 52 and 53

<400> SEQUENCE: 30
tacgctgatt ggattacgca tgggcccatg cgtaatccaa tcagcgtacg atatcg        56

<210> SEQ ID NO 31
<211> LENGTH: 88
<212> TYPE: DNA
<213> ORGANISM: artificial
<220> FEATURE:
<223> OTHER INFORMATION: random

<400> SEQUENCE: 31
aaactgcctc caatgacatt gtccctccca cagggtcttt tgaccctgtg ggagggacaa    60
tgtcattgga ggcagtttcc cttttggg                                       88

<210> SEQ ID NO 32
<211> LENGTH: 19
<212> TYPE: DNA
<213> ORGANISM: Artificial Sequence
<220> FEATURE:
<223> OTHER INFORMATION: decoy

<400> SEQUENCE: 32
uccatgattg gattaccuc                                                 19

<210> SEQ ID NO 33
<211> LENGTH: 19
<212> TYPE: DNA
<213> ORGANISM: Artificial Sequence
<220> FEATURE:
<223> OTHER INFORMATION: decoy

<400> SEQUENCE: 33
acgctgattg gattacgca                                                 19

<210> SEQ ID NO 34
<211> LENGTH: 82
<212> TYPE: DNA
<213> ORGANISM: Artificial Sequence
<220> FEATURE:
<223> OTHER INFORMATION: decoy

<400> SEQUENCE: 34
gcaugggauu ctgcctccat gattggatta cctcccacag gctgcctcca tgattggatt    60
acctcccaca gguaucguac gc                                             82

<210> SEQ ID NO 35
<211> LENGTH: 82
<212> TYPE: DNA
<213> ORGANISM: Artificial Sequence
<220> FEATURE:
```

<223> OTHER INFORMATION: decoy

<400> SEQUENCE: 35

| gcguacgaua cctgtgggag gtactcctat gatggaggca gcctgtggga ggtactccta | 60 |
| tgatggaggc agaaucccau gc | 82 |

<210> SEQ ID NO 36
<211> LENGTH: 82
<212> TYPE: DNA
<213> ORGANISM: Artificial Sequence
<220> FEATURE:
<223> OTHER INFORMATION: decoy

<400> SEQUENCE: 36

| gcaugggauu ctgcctccat cataggagta cctcccacag gctgcctcca tcataggagt | 60 |
| acctcccaca gguaucguac gc | 82 |

<210> SEQ ID NO 37
<211> LENGTH: 88
<212> TYPE: DNA
<213> ORGANISM: Artificial Sequence
<220> FEATURE:
<223> OTHER INFORMATION: decoy

<400> SEQUENCE: 37

| aaactgcctc catcatagga gtacctccca cagggtcttt tgaccctgtg ggaggtactc | 60 |
| ctatgatgga ggcagtttcc cttttggg | 88 |

<210> SEQ ID NO 38
<211> LENGTH: 99
<212> TYPE: DNA
<213> ORGANISM: Artificial Sequence
<220> FEATURE:
<223> OTHER INFORMATION: decoy

<400> SEQUENCE: 38

| tcgagtgatt ggattaccat gattcaatta cctgattcaa ttaccatgat tcaattatct | 60 |
| tgattggatt atgattaaat taatttgatt gggttattc | 99 |

<210> SEQ ID NO 39
<211> LENGTH: 99
<212> TYPE: DNA
<213> ORGANISM: Artificial Sequence
<220> FEATURE:
<223> OTHER INFORMATION: decoy

<400> SEQUENCE: 39

| tcgagcgcat gggattatcg tacgctgatt ggattacgca tgggattatc gtacgctgat | 60 |
| tggattacgc atgggattat cgtacgctga ttaaattac | 99 |

<210> SEQ ID NO 40
<211> LENGTH: 62
<212> TYPE: DNA
<213> ORGANISM: Artificial Sequence
<220> FEATURE:
<223> OTHER INFORMATION: decoy

<400> SEQUENCE: 40

| ctgcctccat gattggatta cctcccacag gctgcctcca tgattggatt acctcccaca | 60 |
| gg | 62 |

The invention claimed is:

1. A viral vector comprising a DUX4 decoy nucleic acid, wherein said DUX4 decoy nucleic acid comprises one or more DUX4 binding sites.

2. The viral vector according to claim 1, wherein said DUX4 decoy nucleic acid comprises 2, 3, 4, 5 or more than 5 DUX4 binding sites.

3. The viral vector according to claim 1, wherein the DUX4 binding site(s) is(are) of the sequence TAAYYBAATCA (SEQ ID NO:1) or TAAYBYAATCA (SEQ ID NO:2).

4. The viral vector according to claim 2, wherein the DUX4 binding site(s) is(are) of the sequence TAAYYBAATCA (SEQ ID NO:1) or TAAYBYAATCA (SEQ ID NO:2).

5. The viral vector according to claim 1, wherein the DUX4 binding site(s) is selected in the group consisting of TAACCCAATCA (SEQ ID NO:3), TAATTTAATCA (SEQ ID NO:4), TAATCCAATCA (SEQ ID NO:5) and TAATTGAATCA (SEQ ID NO:6).

6. The viral vector according to claim 2, wherein the DUX4 binding site(s) is selected in the group consisting of TAACCCAATCA (SEQ ID NO:3), TAATTTAATCA (SEQ ID NO:4), TAATCCAATCA (SEQ ID NO:5) and TAATTGAATCA (SEQ ID NO:6).

7. The viral vector according to claim 1, wherein the decoy nucleic acid comprises a sequence of any one of SEQ ID NO:7 to 28.

8. The viral vector according to claim 1, wherein the decoy nucleic acid consists of a sequence of any one of SEQ ID NO:7 to 28.

9. The vector according to claim 1, wherein the viral vector is a lentiviral vector or an AAV vector.

10. The vector according to claim 2, wherein the viral vector is a lentiviral vector or an AAV vector.

11. The vector according to claim 3, wherein the viral vector is a lentiviral vector or an AAV vector.

12. The vector according to claim 4, wherein the viral vector is a lentiviral vector or an AAV vector.

13. The vector according to claim 5, wherein the viral vector is a lentiviral vector or an AAV vector.

14. The vector according to claim 6, wherein the viral vector is a lentiviral vector or an AAV vector.

15. The vector according to claim 7, wherein the viral vector is a lentiviral vector or an AAV vector.

16. The vector according to claim 8, wherein the viral vector is a lentiviral vector or an AAV vector.

17. A pharmaceutical composition comprising the viral vector of claim 1 and a pharmaceutically or physiologically acceptable carrier.

18. A method of treating FSHD in a subject in need thereof, comprising the administration of a therapeutically effective amount of the viral vector according to claim 1 to said subject.

19. A method of treating FSHD in a subject in need thereof, comprising the administration of a therapeutically effective amount of the viral vector according to claim 7 to said subject.

20. A method of treating FSHD in a subject in need thereof, comprising the administration of a therapeutically effective amount of the viral vector according to claim 8 to said subject.

* * * * *